(12) United States Patent
Mustaev et al.

(10) Patent No.: US 9,586,907 B2
(45) Date of Patent: *Mar. 7, 2017

(54) ISOTHIOCYANATE COMPOUNDS, PHARMACEUTICAL COMPOSITIONS, AND USES THEREOF

(71) Applicant: Rutgers, The State University of New Jersey, New Brunswick, NJ (US)

(72) Inventors: Arkady Mustaev, New York, NY (US); Natalia Kurepina, Fort Lee, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/512,884

(22) Filed: Oct. 13, 2014

(65) Prior Publication Data

US 2015/0246887 A1   Sep. 3, 2015

Related U.S. Application Data

(62) Division of application No. 12/307,724, filed as application No. PCT/US2007/072998 on Jul. 6, 2007, now Pat. No. 8,859,798.

(60) Provisional application No. 60/819,229, filed on Jul. 6, 2006.

(51) Int. Cl.
| | | |
|---|---|---|
| *A61K 31/26* | (2006.01) | |
| *C07C 331/00* | (2006.01) | |
| *A61K 31/21* | (2006.01) | |
| *C07D 233/64* | (2006.01) | |
| *C07C 331/20* | (2006.01) | |
| *C07C 331/22* | (2006.01) | |
| *C07C 331/30* | (2006.01) | |
| *C07C 331/28* | (2006.01) | |
| *C07D 209/14* | (2006.01) | |
| *C07D 213/24* | (2006.01) | |

(52) U.S. Cl.
CPC .......... *C07D 233/64* (2013.01); *C07C 331/20* (2013.01); *C07C 331/22* (2013.01); *C07C 331/28* (2013.01); *C07C 331/30* (2013.01); *C07D 209/14* (2013.01); *C07D 213/24* (2013.01); *C07C 2103/20* (2013.01); *C07C 2103/50* (2013.01); *C07C 2103/74* (2013.01)

(58) Field of Classification Search
CPC ... C07C 331/20; C07C 331/30; C07D 209/14; C07D 213/14; C07D 233/06
See application file for complete search history.

(56) References Cited

U.S. PATENT DOCUMENTS 3,860,573 A * 1/1975 Honkanen .......... C08B 37/0039
528/52
3,887,542 A * 6/1975 Perrella ................ C07D 499/00
540/306

OTHER PUBLICATIONS

Mutalik et al ., Ann. Trop. Med. Parasit. 1970, vol. 647, No. 1, pp. 79-85.*

* cited by examiner

*Primary Examiner* — Savitha Rao
(74) *Attorney, Agent, or Firm* — Fox Rothschild LLP

(57) ABSTRACT

Provided herein are compositions of matter and pharmaceutical compositions thereof, for use in inhibiting the growth of various microbial pathogens, including bacteria, fungi, protozoa, and viral pathogens. Also provided herein are methods of treating microbial diseases/infections and cancer with the compositions. The compositions are additionally useful in wood preservation and food preservation by inhibition of microbial growth.

17 Claims, 7 Drawing Sheets

ISOTHIOCYANATE COMPOUNDS, PHARMACEUTICAL COMPOSITIONS, AND USES THEREOF

CROSS-REFERENCE TO RELATED APPLICATIONS

This application is a divisional of U.S. patent application Ser. No. 12/307,724, filed on Jul. 14, 2009, now U.S. Pat. No. 8,859,798 which is the U.S. National Stage of International Application No. PCT/US07/072998, filed Jul. 6, 2007, which claims priority under 35 U.S.C. §119(e) to U.S. Provisional Application Ser. No. 60/819,229 filed on Jul. 6, 2006, the disclosures of which are incorporated herein by reference in their entirety.

BACKGROUND

The treatment of microbial infections is increasingly complicated by the ability of certain microbes (e.g., bacteria) to develop resistance to anti-microbial agents.

Of particular concern are hospital-contracted, or nosocomial infections, which exhibit antibiotic resistance. *Streptococcus pneumoniae*, for example, causes approximately 3,000 cases of meningitis, 50,000 cases of bacteremia, 500,000 cases of pneumonia, and nearly 7,000,000 cases of otitis media in the United States, in addition to being a leading cause of mortality. Antibiotic resistant strains of *Streptococcus* have emerged and are now becoming widespread in certain communities. While vancomycin remains effective at treating the vast majority of *Streptococcus* infections, vancomycin resistant strains have already been identified (see, for example, Archer et al. (1994) Antimicrob. Agents Chemother. 33(4):791-793).

*Escherichia coli* O157:H7 (herein referred to as O157:H7) is an emerging cause of food borne illness. The CDC estimates that there are approximately 73,000 cases of infection and 61 deaths in the United States each year. Infection has a range of consequences from bloody diarrhea to occasional kidney failure. Most illness has been associated with eating undercooked, contaminated ground beef. Infection can also occur after drinking unpasteurized milk. In addition, other microbial pathogens, such as *Salmonella, Shigella, Listeria,* and *Campylobacter,* are also potential food product contaminants and are known to cause serious disease in humans (Tauxe R. V. (2002) Int. J. Food Microbiol. 78(1-2):31-41; Mead et al. (1999) Emerg. Infect. Dis. 5(5):607-625). At present there is no effective conventional antibiotic treatment for O157:H7, and drug-resistant *Campylobacter* infections (for example, macrolide-resistant *Campylobacter*) are becoming increasingly common (Gibreel et al. (2006) J. Antimicrob. Chemother. May 30). While one strategy to combat food contamination has been to add antibiotics to livestock feed, this has resulted in high levels of antibiotic resistant bacteria which ultimately endangers both livestock and humans. In addition, such antibiotic resistance decreases the value of certain antibiotics for use in humans (Phillips et al. (2004) J. Antimicrob. Chemother. 53(1):28-52).

Thus, not only is there a need for new antibiotics which can treat specific, drug-resistant nosocomial (e.g., *Streptococcus*) and food-borne pathogens (e.g., O157:H1 and *Campylobacter*), but also for alternative strategies for preventing or destroying microbial infections of food, for example, through direct treatment of food products.

Glucosinolates and their breakdown products—isothiocyanates (ITCs) are secondary metabolites, actively used by certain plants for the defense against natural pathogens (Fenwick et al. (1983) Crit. Rev. Food Sci. Nutr. 18:123-201; Delaquis et al. (1995) Food Technol. 73-84; Osbourn et al. (1996) Plant Cell 8:1821-1831; Fahey et al. (2001) Phytochemistry 56:5-51). These compounds are commonly found in and enriched in the plant family Cruciferae, which includes, for example, broccoli, cabbage, watercress, and Brussel sprouts). These vegetables are widely consumed by humans.

Despite their history of use in folk medicine, evaluation of ITCs as potential anti-pathogens has been limited, potentially due to relatively low activity of test compounds (Tajima et al. (2001) Biosci. Biotechnol. Biochem. 65:1886-1888; Tajima et al. (2003) Biosci. Biotechnol. Biochem. 67:1844-1846; and Fahey et al. (2002) Proc. Natl. Acad. Sci. USA 99:7610-7615).

SUMMARY

This invention is based, in part, on the generation of novel compositions of matter (e.g., novel ITC compounds) that possess anti-microbial and anti-cancer activity. Provided herein are the compositions of matter (e.g., ITC compounds) that have anti-microbial and anti-cancer activity and pharmaceutical compositions thereof (including oral formulations of the anti-microbial compounds useful in the prevention or reduction of the formation of dental plaque). In addition, provided herein are methods in which such compositions are useful, including, methods for inhibiting the growth of a cell, methods for treating an infection or a cancer in a subject, and methods of food and wood preservation.

Provided herein are compositions of matter having the Formula I:

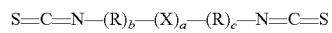

$$S=C=N-(R)_b-(X)_a-(R)_c-N=C=S$$

or pharmaceutically acceptable salts or derivatives thereof, where a, b, and c are independently 0 or 1, provided that a, b, and c are not all 0;

X is an aryl or heteroaryl ring system which may be unsubstituted or substituted with from 1 to 4 moieties selected from —Br, —Cl, —OH, —NH$_2$, —COOH, OR'—CH$_3$ or R"—CH$_3$ wherein R' and R", independently, are an alkylene moiety having the formula —(CH$_2$)$_n$—, where n can be an integer from 0 to 20; and each R, independently, is selected from the group consisting of linear or branched alkylene, alkenylene, and alkynylene moieties having from 1 to 20 C atoms; linear or branched heteroalkylene moieties having from 2 to 20 C atoms and from 1 to 3 O, N or S atoms; and arylene, heteroarylene, and cycloalkylene moieties having from 5 to 10 C atoms and from 1 to 3 N, S, or O atoms.

In some embodiments, the composition has the formula I where X can be selected from phenyl, biphenyl, napthyl, anthrocyl, indole, pyrimidine, pyrene, furan, and pyridine. The compositions can also have the formula I where each R, independently, can be an alkylene moiety having the formula —(CH$_2$)$_n$—, and where n can be an integer from 1 to 20.

In another embodiment, the composition can have the formula I where a and b are 0, c is 1, R is an alkylene moiety having the formula —(CH$_2$)$_n$— and n is 4, 5, 6, 7, or 8. The composition can also have the formula I and the chemical structure of compounds 38, 39, 40, 41, or 42 of Table 1.

In some embodiments, where X is a phenyl ring, the composition can have the formula I where a, b and c are 1, and R is, independently, an alkylene moiety having the formula —$(CH_2)$—. The compound can also have the formula I and the chemical structure of compound 37 of Table 1.

In another embodiment, the composition can have the formula I where c is 0, a and b are 1, and R is an alkylene moiety having the formula —$(CH_2)$—. The composition can also have the formula I and the chemical structure of compound 16 of Table 1.

In another embodiment, the composition can have the formula I where a and b are 0, c is 1, and R is, independently, an heteroalkylene moiety having the formula —$(CH_2)_2$—O—$(CH_2)_2$—O—$(CH_2)_2$—. The composition can also have the formula I and the chemical structure of compound 43 of Table 1.

Also provided herein are compositions of matter having the formula II:

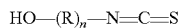
HO—$(R)_n$—N=C=S where R is an alkylene group having the formula —$(CH_2)$—, and n is an integer from 7-20.

In one embodiment, the composition has formula II where n is 7 or 8. In some embodiments, the composition has the formula II and the chemical structure of Compound 44 or 45 of Table 1.

Also provided herein are compositions having the formula III:

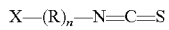
X—$(R)_n$—N=C=S wherein X is pyrimidine ring, where R is conjugated to the pyrimidine ring at any position 2-6 in the ring, and wherein the pyrimidine ring may be further substituted at any position with one or more moieties selected from —Br, —Cl, —OH, —$NH_2$, —COOH, OR'—$CH_3$ or R"—$CH_3$ wherein R' and R", independently, are an alkylene moiety having the formula —$(CH_2)_{n'}$—, where n' can be an integer from 0 to 20; and where R is selected from the group consisting of linear or branched alkylene, alkenylene, and alkynylene moieties having from 1 to 20 C atoms; linear or branched heteroalkylene moieties having from 2 to 20 C atoms and from 1 to 3 O, N or S atoms; and arylene, heteroarylene, and cycloalkylene moieties having from 5 to 10 C atoms and from 1 to 3 N, S, or O atoms.

In one embodiment, the composition can have the formula III where R can be at position 3 or position 2 of the pyrimidine ring. The composition can have formula I where R is an alkylene moiety having the formula —$CH_2$—, and n is 1. The composition can also have the formula III and the chemical structure of compound 30 of Table 1.

In another embodiment, the composition has the formula III where R is a heteroalkylene moiety having the formula —$CH_2$—O—$CH_2$—, and n is 1. In some embodiments, the composition has the formula III and the chemical structure of compound 31 or 32 of Table 1.

Also provided herein are compositions of matter having the formula IV:

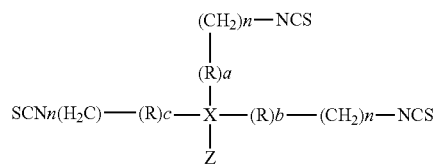

where X can be C, N, or P, provided that if X is N or P, Z is not present;

each n can range independently from 0 to 20;
a, b, and c can be independently 0 or 1, provided that if a, b, or c is 0, then the n of the adjacent —$(CH_2)_n$— moiety is not 0;
each R can be independently selected from the group consisting of alkylene, heteroalkylene, arylene, heteroarylene, and cycloalkylene moieties having from 5 to 10 C atoms and from 1 to 3 N, S, or O atoms; and
Z can be selected from —Br, —Cl, —OH, —$NH_2$, —COOH, OR'—$CH_3$ or R"—$CH_3$ wherein R' and R", independently, are an alkylene moiety having the formula —$(CH_2)_{n'}$—, where n' can be an integer from 0 to 20, and $(CH_2)_m$—NCS, where m can range from 1 to 20.

In some embodiments, the composition can have the formula IV where X is N, P or C. In another embodiment, the composition can have the formula IV where R is a phenyl moiety. In another embodiment, the composition can have the formula IV where a, b, and c are 0.

In some embodiments, the composition has formula IV where R is a phenyl moiety, a, b, and c are 0, and Z is $(CH_2)_m$—N=C=S.

Also provided herein are compositions of matter having the formula V:

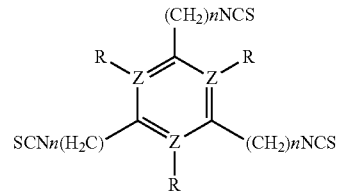

where each Z, independently, is C or N;
each R, independently, is selected from —H and —Br, —Cl, —OH, —$NH_2$, —COOH, OR'—$CH_3$ or R"—$CH_3$ wherein R' and R", independently, are an alkylene moiety having the formula —$(CH_2)_{n'}$— where n' can be an integer from 0 to 20; and
each n can range independently from 0 to 20.

In some embodiments, the composition has the formula V, where Z is N, and R is —H. In another embodiment, the composition has the formula V where Z is C.

Also provided herein are compositions of matter having the formula VI:

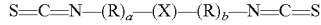
S=C=N—$(R)_a$—(X)—$(R)_b$—N=C=S where a and b can be independently 0 or 1;
X can be an S, thionyl, or sulfuryl moiety; and
and each R, independently, is selected from —H and —Br, —Cl, —OH, —$NH_2$, —COOH, OR'—$CH_3$ or R"—$CH_3$ wherein R' and R", independently, are an alkylene moiety having the formula —$(CH_2)_{n'}$—, where n' can be an integer from 0 to 20; and
each n can range independently from 0 to 20.

In some embodiments, the composition has the formula VI where X is a thionyl or a sulfuryl moiety.

Also provided herein are compositions of matter having the formula VII:

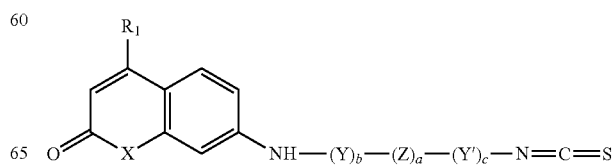

where a, b, and c are 1 or 0;

X is a C, O, or N atom;

Y or Y', independently, is a alkylene moiety having the formula ($-CH_2$)$_n$—, wherein n is an integer from 1 to 20;

Z is an aryl or heteroaryl ring system which may be unsubstituted or substituted with from 1 to 4 moieties selected from —Br, Cl, —F, —OH, —NH2, —COOH, —OR'—CH3, R"—CH3, wherein R' and R", independently, are an alkylene moiety having the formula —($CH_2$)$_n$—, where n can be an integer from 0 to 20;

$R_1$ is an H; NH; a linear or branched alkylene moiety having from 1 to 20 C atoms, and can be substituted with 1 to 3 halo moieties; or a linear or branched heteroalkylene moiety having from 1 to 3 N atoms, 1 to 20 C atoms, and 1 to 4 O atoms.

In one embodiment, the composition can have the formula VII where X is O.

In another embodiment, the composition can have the formula VII where X is C or N. In a related embodiment, the composition can have the formula VII where $R_1$ is $CH_3$ or $CF_3$.

In another embodiment, the composition has the formula VII where a, b, and c are 1. The composition can also have formula I, where a and b are 0, and c is 1.

In another embodiment, the composition can have the formula VII where Y or Y' is an alkylene moiety having the formula —($CH_2$)$_n$— and n is 6. The composition can have the formula VII where Z is a phenyl ring.

In certain embodiments, the composition can have the formula VII and the chemical structure of compound 58, 67, 68, or 69 of FIG. 5.

Also provided are pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Further provided are pharmaceutical compositions containing the compounds provided herein and a pharmaceutically acceptable carrier. In one embodiment, the pharmaceutical compositions are formulated for single dosage administration.

Also provided herein are methods of treating a subject infected with, or likely of becoming infected with, a microbial pathogen. The method involves delivering to a subject an anti-microbially effective amount of the pharmaceutical compositions described herein. The method can, optionally, involve an initial diagnostic step of determining whether the subject has an infection with a microbial pathogen. The subject can be any organism that is susceptible to infection by a microbe (e.g., a worm, a plant, an insect, a frog, a lizard, or a fish). The subject can also be a mammal (e.g., a mouse, rat, guinea pig, hamster, gerbil, dog, cat, horse, cow, sheep, goat, monkey, or a whale). The subject can also be a human (e.g., a human patient). In some embodiments, the microbial infections that can be treated by the above-described method is caused by a bacterium. The bacterium can be gram-positive or gram-negative. The gram-positive bacterium can be one or more of the following: *Bacillus cereus, Bacillus subtilis, Staphylococcus epidermis, Staphylococcus aureus, Streptococcus pyogenes, Enterococcus faecium, Enterococcus faecalis, Mycobacterium tuberculosis, Mycobacterium avium, Mycobacterium bovis, Micrococcus luteus*, and *Bacillus anthracis*. The gram-negative bacterium can be one or more of the following: *Haemophilus ducreyi, Neisseria gonorrheae, Klebsiella pneumoniae*, or *Psuedomanas aeruginosa*. The bacterium can also be a drug-resistant bacterium (e.g., a bacterium which has acquired resistance to an antibiotic, for example, Methicillin, Erythromycin, Oxacillin, Gentamycin, Vancomycin, Ampicillin, Ioniazid, Rifampicin, or Ciprofloxacin). The bacterium can also be multidrug resistant (e.g., resistant to more than one of any of the antibiotics described above or additional antibiotics). The antibiotic resistant bacterium can be one of the following: Methicillin resistant *Staphylococcus aureus*, Erythromycin resistant *Staphylococcus aureus*, Oxacillin/Gentamycin resistant *Staphylococcus aureus*, Vancomycin/Oxacillin resistant *Staphylococcus aureus*, Gentamycin resistant *Enterococcus faecium*, Vancomycin resistant *Enterococcus faecium*, Ampicillin-resistant *Enterococcus faecium*, Gentamycin resistant *Enterococcus faecalis*, Vancomycin resistant *Enterococcus faecalis*, Ampicillin-resistant *Enterococcus faecalis*, Rifampicin resistant *Mycobacterium tuberculosis*, Isoniazid resistant *Mycobacterium tuberculosis*, multidrug resistant *Mycobacterium tuberculosis*, or Rifampicin resistant *Mycobacterium bovis*.

Also featured herein for use in the above-described method are pharmaceutical compositions containing the compounds 37, 40, 41, and 42 of Table 1.

The microbial infection can also be a fungal infection. The fungus can be one or more of the following: *Aspergillus fumigatus, Candida glabrata, Candida albicans, Candida glabrata, Candida crusei, Candida parapsilosis*, and *Cryptococcus neoformans*.

The microbial infection which can be treated by the method described herein can also be a protozoan infection. The protozoan can be any one or more of the following: *Endamoeba hartmanii, Dientamoeba fragilis, Giardia lamblia, Balantidium coli, Toxoplasma gondii, Giardia duodenalis, Entamoeba histolytica, Cryptosporidium parvum, Cyclospora cayetanensis, Isospora belli, Leishmania braziliensis, Leishmania tropica, Leishmania infantum, Leishmania amazonensis, Plasmodium vivax, Plasmodium ovale*, and *Microsporidia*.

Of particular use in the methods for treating fungal or protozoan infections, are pharmaceutical compositions containing compound 37 of Table 1.

Also embraced by the method, are embodiments where a subject is infected with one or more of a particular microbe (e.g., two different bacterial strains or species) or one or more kinds of microbe (e.g., an infection with bacteria and fungus). Such subjects can be, for example, immunocompromised subjects, (e.g., human patients with HIV-1 or AIDS). The methods of treatment can involve delivering one or more anti-microbial compositions to the subject. The additional composition can be another composition described herein, or can be, for example, another antibiotic or therapeutic or prophylactic composition, such as ampicillin.

Also featured herein is a method of inhibiting the growth of a cell by contacting the cell with a growth-inhibitory amount of a composition containing any of the compositions described herein. In some embodiments, the cell can be a bacterial cell. The bacterial cell can be gram-positive or gram-negative. The gram-positive bacterial cell can be any one of the following: *Bacillus cereus, Bacillus subtilis, Staphylococcus epidermis, Staphylococcus aureus, Streptococcus pyogenes, Enterococcus faecium, Enterococcus faecalis, Mycobacterium tuberculosis, Mycobacterium avium, Mycobacterium bovis*, or *Bacillus anthracis*. The gram-negative bacterial cell can be any one of the following: *Haemophilus ducreyi, Neisseria gonorrheae, Klebsiella pneumoniae*, or *Psuedomanas aeruginosa*.

The bacterial cell inhibited by the method, in some embodiments, can be a drug resistant bacterial cell. The drug resistant bacterial cell can be resistant to one or more of a variety of antibiotics such as, for example, Methicillin, Erythromycin, Oxacillin, Gentamycin, Vancomycin, Ampicillin, Ioniazid, Rifampicin, or Ciprofloxacin. In some embodiments, the drug resistant bacterial cell can be one or more of: Methicillin resistant *Staphylococcus aureus*, Erythromycin resistant *Staphylococcus aureus*, Oxacillin/Gentamycin resistant *Staphylococcus aureus*, Vancomycin/Oxacillin resistant *Staphylococcus aureus*, Gentamycin resistant *Enterococcus faecium*, Vancomycin resistant *Enterococcus faecium*, Ampicillin-resistant *Enterococcus faecium*, Gentamycin resistant *Enterococcus faecalis*, Vancomycin resistant *Entercoccus faecalis*, Ampicillin-resistant *Enterococcus faecalis*, Rifampicin resistant *Mycobacterium tuberculosis*, Isoniazid resistant *Mycobacterium tuberculosis*, multidrug resistant *Mycobacterium tuberculosis*, or Rifampicin resistant *Mycobacterium bovis*.

In another embodiment, a cell inhibited by the above-described method can be a fungal cell. In some embodiments, the fungal cell can be: *Aspergillus fumigatus, Candida glabrata, Candida albicans, Candida glabrata, Candida crusei, Candida parapsilosis*, and *Cryptococcus neoformans*.

In another embodiment, a cell inhibited by the above-described method can be a protozoan cell. In some embodiments, the protozoan cell can be: *Endamoeba hartmanii, Dientamoeba fragilis, Giardia lamblia, Balantidium coli, Toxoplasma gondii, Giardia duodenalis, Entamoeba histolytica, Cryptosporidium parvum, Cyclospora cayetanensis, Isospora belli, Leishmania braziliensis, Leishmania tropica, Leishmania infantum, Leishmania amazonensis, Plasmodium vivax, Plasmodium ovale*, and *Microsporidia*.

In another embodiment, a cell inhibited by the method described herein can be a cancer cell. In some embodiments, the cancer cell can be a human cancer cell of any type (e.g., colon, breast, prostate, lung, liver, kidney, pancreas, or brain). In certain embodiments, the human cancer cell can be a liquid tissue cancer, for example, a leukemia or lymphoma, In one embodiment, the method of inhibiting the growth of a cell is an in vitro method. In another embodiment, the method of inhibiting the growth of a cell is an in vivo method.

Also featured herein is a method of treating a subject having, or likely to develop, a cancer. The method involves delivering to a subject a therapeutically effective amount of a composition with an active ingredient containing any of the compositions described herein. The method can, optionally, include an additional step of testing (e.g., determining, detecting, monitoring, assaying) whether the subject has a cancer. In some embodiments, the subject can be a mammalian subject (e.g., a mouse, rat, guinea pig, hamster, gerbil, dog, cat, horse, cow, sheep, goat, monkey, a whale, or a human (e.g., a human patient)). In some embodiments, a cancer in a subject treated by the method can be a lung, colon, prostate, or breast cancer.

The treatment method can also, optionally, involve administering one or more additional anti-cancer compositions to the subject. In some embodiments, the additional anti-cancer composition is one or more of an additional composition of matter described herein. The additional anti-cancer composition is one or more of the following chemotherapeutics: cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-flurouracil, vincristin, vinblastin, methotrexate, Herceptin, and an analog of any of the aforementioned.

In the above-mentioned cancer-treating method any one of the compositions described herein can be delivered in combination with radiation therapy (e.g., gamma-irradiation).

Also featured herein are any of the compositions described herein for use as a medicament. In some embodiments, the compositions for use as a medicament can be those compositions of matter having formulas I, IV, V, VI, and VII.

Also featured herein are any of the compositions described herein for use in the manufacture of a medicament for the therapeutic and/or prophylactic treatment of a subject having, or likely to develop, a microbial infection. The compositions for use in the manufacture of a medicament for the therapeutic and/or prophylactic treatment of a subject having, or likely to develop, a microbial infection can be the compositions of matter having formulas I, VI, V, VI, and VII.

In some embodiments of the use described above, the subject can be a mammal (e.g, a mouse, rat, guinea pig, hamster, gerbil, dog, cat, horse, cow, sheep, goat, monkey, or a whale). In some embodiments, the subject is a human, (e.g, a human patient). Also embraced by the method are microbial infections in a subject, where the microbial infection is a bacterial infection. The bacterial infection can be caused by, for example, a gram-positive or gram-negative bacterium. The gram-positive bacterium can be: *Bacillus cereus, Bacillus subtilis, Staphylococcus epidermis, Staphylococcus aureus, Streptococcus pyogenes, Enterococcus faecium, Enterococcus faecalis, Mycobacterium tuberculosis, Mycobacterium avium, Mycobacterium bovis*, or *Bacillus anthracis*. The gram-negative bacterium can be: *Haemophilus ducreyi, Neisseria gonorrheae, Klebsiella pneumoniae*, or *Psuedomanas aeruginosa*. The bacterial infection can also be an infection caused by a drug-resistant bacterium. The bacterium can be resistant to, without limitation, one or more of the following antibiotics: Methicillin, Erythromycin, Oxacillin, Gentamycin, Vancomycin, Ampicillin, Ioniazid, Rifampicin, or Ciprofloxacin. In some embodiments, the drug resistant bacterium can be: Methicillin resistant *Staphylococcus aureus*, Erythromycin resistant *Staphylococcus aureus*, Oxacillin/Gentamycin resistant *Staphylococcus aureus*, Vancomycin/Oxacillin resistant *Staphylococcus aureus*, Gentamycin resistant *Enterococcus faecium*, Vancomycin resistant *Entercoccus faecium*, Ampicillin-resistant *Enterococcus faecium*, Gentamycin resistant *Enterococcus faecalis*, Vancomycin resistant *Entercoccus faecalis*, Ampicillin-resistant *Enterococcus faecalis*, Rifampicin resistant *Mycobacterium tuberculosis*, Isoniazid resistant *Mycobac-*

*terium tuberculosis*, multidrug resistant *Mycobacterium tuberculosis*, or Rifampicin resistant *Mycobacterium bovis*.

In another embodiment, the microbial infection can be a fungal infection. The fungal infection can be an infection of a subject by any one of the following fungal organisms: *Aspergillus fumigatus, Candida glabrata, Candida albicans, Candida glabrata, Candida crusei, Candida parapsilosis*, and *Cryptococcus neoformans*. In another embodiment, the microbial infection is a protozoal infection. The protozoal infection can be an infection of a subject by any one of the following protozoal organisms: *Endamoeba hartmanii, Dientamoeba fragilis, Giardia lamblia, Balantidium coli, Toxoplasma gondii, Giardia duodenalis, Entamoeba histolytica, Cryptosporidium parvum, Cyclospora cayetanensis, Isospora belli, Leishmania braziliensis, Leishmania tropica, Leishmania infantum, Leishmania amazonensis, Plasmodium vivax, Plasmodium ovale*, and *Microsporidia*.

Also featured herein are compositions for the prophylactic and therapeutic treatment of microbial dental caries and microbial periodontal disease. These compositions contain an anti-microbially-effective amount of any of the compositions or pharmaceutical compositions thereof described herein and a carrier for delivering the composition to the mouth, the gums, or the teeth. The dental caries or periodontal disease treatable with the above-described compositions can be a sore, a cavity, gingivitis, periodontitis (mild, moderate, or advanced), or dental plaque.

In one embodiment of the compositions, the carrier is a toothpaste. In another embodiment, the carrier can be a chewing gum, an ointment, cream, mouth wash, mouth rinse, or a lozenge.

Also featured herein is a method of inhibiting the formation of dental plaque on the teeth of a subject by delivering to the teeth the above-described compositions and an oral carrier (e.g., toothpaste, gum, ointment, cream, lozenge, mouth wash, or mouth rinse). In some embodiments, the method can, optionally, involve a step of identifying a subject as having a dental plaque already, in which case the delivering would prevent further formation.

In some embodiments, the dental plaque is caused by *Lactobacillus* or *Streptococcus*.

In some embodiments of the method, the subject is a mammal (e.g., a mouse, rat, guinea pig, hamster, gerbil, dog, cat, horse, cow, sheep, goat, monkey, or a whale). In another embodiment, the mammal is a human (e.g, a human patient).

Also featured herein is a method of treating bacterial gastritis in a subject. The method involves delivering to a subject with a bacterial-induced gastritis a pharmaceutical composition containing any of the compositions of matter described herein. In some embodiments, the method, optionally, includes a step of identifying a subject as having a bacterial-induced gastritis. In some embodiments of the method, the subject can be a mammal (e.g., a mouse, rat, guinea pig, hamster, gerbil, dog, cat, horse, cow, sheep, goat, monkey, or a whale). In another embodiment, the mammal is a human (e.g., a human patient).

In some embodiments, the bacterial-induced gastritis of the invention can be induced by *Helicobacter pylori*.

Also featured herein are compositions for wood preservation containing any of the compositions of matter described herein. The wood-preserving compositions can be particularly useful for the wood-preserving methods described below.

Also provided herein is a method of wood preservation by delivering (e.g., contacting or administering) to a wood any of the compositions described herein or the wood-preserving compositions above. In some embodiments, the wood is a wood piling, a structural timber (e.g., the wooden portion of a bridge, or a wooden utility pole), or a wood in contact with soil.

Also provided herein is a composition for use in food preservation, which includes any of the compositions of matter described herein. The food-preserving compositions can be particularly useful for the food-preserving methods described below.

Also provided herein is a method for preserving food. This method includes a step of contacting the food with the food preserving composition described above. For both food preservation composition and method, the food can be any food product (e.g., liquid or solid) consumed by an organism. The organism includes, for example, multicellular organisms such as nematodes, insects, and reptiles. The organism can also be a mammal (e.g., a mouse, rat, guinea pig, hamster, gerbil, dog, cat, horse, cow, sheep, goat, monkey, a whale, or a human).

The details of one or more embodiments of the invention are set forth in the accompanying drawings and the description below. Other features, objects, and advantages of the invention will be apparent from the description and drawings, and from the claims. All cited patents, patent applications, and references are incorporated by reference in their entireties for all purposes.

In case of conflict, the present specification, including definitions, will control. In addition, the materials, methods, and examples are illustrative only and not intended to be limiting.

DETAILED DESCRIPTION

Figure 1:
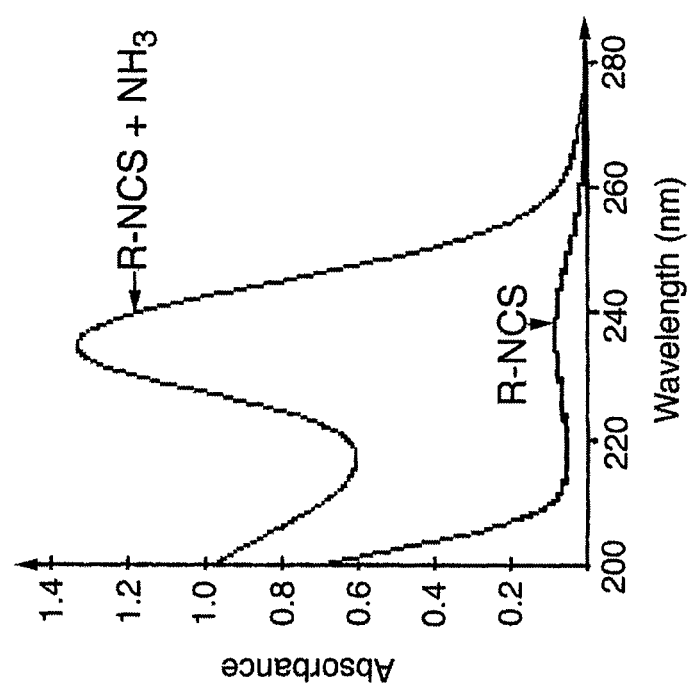
FIG. 1 is a graph depicting the UV absorption spectra of 5-hydroxypentyl-ITC (labled R-NCS, lower curve) and its reaction product with ammonia (labeled R-NCS+NH$_3$, upper curve). The X-axis represents the wavelength of light in nanometers, and the Y-axis is the absorbance measurement.

Featured herein are compositions of matter and pharmaceutical compositions thereof, as well as methods of use for the compositions. Various aspects of the invention are described below.

DEFINITIONS

As used herein, "microbe" or "microbial pathogen" refers to a minute, single cell life form (i.e., a microorganism) that is capable of causing disease in a subject.

As used herein, anti-microbial refers to an ability to kill (i.e., to be cidal) or inhibit the growth (i.e., to be static or induce stasis) of microbes (e.g., microbial pathogens) including, without limitation, bacteria, fungi (including yeasts), and protozoa, or attenuate the severity of a microbial infection of a subject Inhibition of microbial growth can be complete inhibition of growth (i.e., 100% growth arrest). Inhibition of microbial growth can also be, however, less than complete inhibition (e.g., 5%, 10%, 15%, 20%, 25%, 30%, 35%, 40%, 45%, 50%, 55%, 60%, 65%, 70%, 75%, 80%, 85%, 90%, 95%, or up to 99% of complete inhibition of microbial growth). The antimicrobial compounds of the invention are compounds that can be used in the treatment of a microbial disease or infection. As used herein, the term "anti-microbially effective amount" refers to the amount (e.g, the dosage) of any agent (e.g., any of the compositions described herein) required to be anti-microbial when given (e.g., contacted or administered) to the microbe. This amount will vary based on, for example, the individual microbial organism, the subject, or the extent or severity of infection (see, for example, the Detailed Description below). Such inhibition can be determined by a variety of methods well known to those of skill in the art (e.g., those described in detail in the Detailed Description and Examples sections below).

As used herein, treatment or treating means any manner in which one or more of the symptoms of a disease or disorder are ameliorated or otherwise beneficially altered. Treatment also encompasses any pharmaceutical use of the compositions herein, such as use for treating infections caused by certain microbial pathogens (e.g., bacteria, fungi, or protozoa), or for treating cancers. The effect can be prophylactic in terms of completely or partially preventing a disease or symptom thereof (e.g., preventing an infection by a microorganism, preventing cellular internalization of a microorganism) and/or can be therapeutic in terms of a partial or complete cure for a disease (e.g., cancer) or an infection (e.g., a microbial infection) and/or adverse effect (e.g., scarring, fever) attributable to the disease or infection. In the context of microbial infection, treatment and treating include, for example, (i) preventing a microbial disease/infection from occurring in a subject who can be predisposed to but has not yet been diagnosed with a microbial disease or infection (e.g., a subject who was exposed to a microbial pathogen but has not yet developed symptoms of the microbial infection); (ii) inhibiting the progression or transmission of a microbial disease/infection (e.g., arresting the growth of a microbial pathogen (static inhibition)); or (iii) relieving the microbial disease/infection (i.e., resulting in amelioration or regression (i.e., killing of the microbes) of the disease/infection).

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, a "growth-inhibitory amount" is the amount (e.g., the dose) of an agent (e.g., any of the compositions described herein) required to inhibit the growth of a cell when applied (e.g., contacted or administered) to the cell Inhibition of cell growth can be complete inhibition of growth (i.e., 100% growth arrest). Inhibition of cell growth can also be, however, less than complete inhibition of cell growth (e.g., 5%, 10%, 15%, 20%, 25%, 30%, 35%, 40%, 45%, 50%, 55%, 60%, 65%, 70%, 75%, 80%, 85%, 90%, 95%, or up to 99% of complete inhibition of cell growth). Such inhibition can be determined by a variety of methods well known to those of skill in the art (e.g., those described in detail in the Detailed Description and Examples sections below.

As used herein, $IC_{50}$ refers to an amount, concentration or dosage of a particular test compound that achieves a 50% inhibition of a maximal response, such as inhibition of bacterial growth, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the Minimum Inhibitory Concentration (MIC) refers to a measure of the highest dilution (i.e., lowest concentration) of a growth inhibitory compound (e.g., and antibiotic, or anti-cancer agent) that completely inhibits the growth of a cell contacted thereby.

The term "subject" refers to a member of the class Mammalia. Examples of mammals include, without limitation, humans, primates, chimpanzees, rodents, mice, rats, rabbits, horses, livestock, dogs, cats, sheep, and cows. In certain preferred embodiments, the "subject" is a human (e.g., a human patient).

As used herein, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

As used herein, "caries" or "dental caries" refers to the decay of bone or tooth, specifically dental caries (tooth decay), and the formation of cavities or holes in the teeth by the action of microbes (e.g., bacteria).

As used herein, "oral carrier" refers to a substance that facilitates delivery of a medicament or therapeutic or prophylactic composition to various parts of the mouth (e.g., the gums, the teeth, or the tongue). Typical oral carriers include, but are not limited to, tooth pastes, chewing gums, lozenges, topical ointments or creams, mouth washes, coated dental floss or tape, and mouth rinses.

As used herein, pharmaceutically acceptable derivatives of a composition include salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl.

Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, "alkyl," "alkenyl" and "alkynyl" carbon chains, if not specified, contain from 1 to 20 (e.g., 1, 2, 3, 4, 5, 6, 7, 8, 9, 10, 11, 12, 13, 14, 15, 16, 17, 18, 19, or 20; 1-5, 1-6, 1-10, 10-15, 15-20) carbons and are straight, cyclic, or branched. Alkenyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 (e.g., 1, 2, 3, 4, 5, 6, 7, or 8) double bonds and alkenyl carbon chains of 2 to 16 (e.g., 2, 3, 4, 5, 6, 7, 8, 9, 10, 11, 12, 13, 14, 15, or 16) carbons, in certain embodiments, contain 1 to 5 (e.g., 1, 2, 3, 4, or 5) double bonds. Alkynyl carbon chains of from 2 to 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbons, in certain embodiments, contain 1 to 8 triple bonds, and the alkynyl carbon chains of 2 to 16 (e.g., 2, 3, 4, 5, 6, 7, 8, 9, 10, 11, 12, 13, 14, 15, or 16) carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons (e.g., 1, 2, 3, 4, 5, or 6). As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 (e.g., 3, 4, 5, 6, 7, 8, 9, or 10; 3-5, 3-6, 3-8, 5-10) carbon atoms, in other embodiments of 3 to 6 (e.g., 3, 4, 5, or 6) carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 (e.g., 3, 4, 5, 6, 7, 8, 9 or 10; 3-5, 3-7, 5-10) carbon atoms, with cycloalkenyl groups, in further embodiments, containing 4 to 7 (e.g., 4, 5, 6, or 7) carbon atoms and cycloalkynyl groups, in further embodiments, containing 8 to 10 (e.g., 8, 9 or 10) carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 (e.g., 6, 7, 8, 9, 10, 11, 12, 13, 14, 15, 16, 17, 18, or 19; 6-8, 6-10, 6-12, 6-15, 10-15, 15-19) carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 (e.g., 5, 6, 7, 8, 9, 10, 11, 12, 13, 14, or 15; 5-7, 5-9, 5-10, 10-12, 10-15) members where one or more, in one embodiment 1 to 3 (e.g., 1, 2, or 3), of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, "heterocyclyl" refers to a monocyclic or multicyclic non-aromatic ring system, in one embodiment of 3 to 10 (e.g., 3, 4, 5, 6, 7, 8, 9, or 10) members, in another embodiment of 4 to 7 (e.g., 4, 5, 6, or 7) members, in a further embodiment of 5 to 6 members, where one or more, in certain embodiments, 1 to 3 (e.g., 1, 2, or 3), of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$—.

As used herein, "carboxy" refers to a divalent radical, —C(O)O—.

As used herein, "aminocarbonyl" refers to —C(O)NH$_2$.

As used herein, "arylaminocarbonyl" refers to —C(O)NHR in which R is aryl, including lower aryl, such as phenyl.

As used herein, "hydroxycarbonyl" refers to —COOH.

As used herein, "alkylene" refers to a straight, branched or cyclic, in certain embodiments straight or branched, divalent aliphatic hydrocarbon group, in one embodiment having from 1 to about 20 carbon atoms (e.g., 1, 2, 3, 4, 5, 6, 7, 8, 9, 10, 11, 12, 13, 14, 15, 16, 17, 18, 19, or 20, or 1-2, 1-5, 1-10, 6-10, 10-15, or 10-20). In a further embodiment alkylene includes lower alkylene. There may be optionally inserted along the alkylene group one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—(CH$_2$)$_2$—O—). The term "lower alkylene" refers to alkylene groups having 1 to 6 (e.g., 1, 2, 3, 4, 5, or 6) carbons. In certain embodiments, alkylene groups are lower alkylene, including alkylene of 1 to 3 (e.g., 1, 2, or 3) carbon atoms.

As used herein, "alkenylene" refers to a straight, branched or cyclic, in one embodiment straight or branched, divalent aliphatic hydrocarbon group, in certain embodiments having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one double bond, in other embodiments 1 to 12 (e.g., 1, 2, 3, 4, 5, 6, 7, 8, 9, 10, 11, or 12; 1-5, 2-6, 2-10, or10-12) carbons. In further embodiments, alkenylene groups include lower alkenylene. There may be optionally inserted along the alkenylene group one or more oxygen, sulfur or substituted or unsubstituted nitrogen atoms, where the nitrogen substituent is alkyl. Alkenylene groups include, but are not limited to, —CH=CH—CH=CH— and —CH=CH—CH$_2$—. The term "lower alkenylene" refers to alkenylene groups having 2 to 6 (e.g., 2, 3, 4, 5, or 6) carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or substituted or unsubstituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 (e.g., 2, 3, 4, 5, or 6) carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 (e.g., 2, 3, 4, 5, 6, 7, 8, 9, 10, 11, 12, 13, 14, 15, 16, 17, 18, 19, or 20; 2-5, 2-6, 2-10, 10-15, 15-20) carbon atoms and at least one triple bond, and at least one double bond; in another embodiment 1 to 12 (e.g., 1, 2, 3, 4, 5, 6, 7, 8, 9, 10, 11, or 12; 1-5, 2-6, 2-10, or10-12) carbons. In further embodiments, alk(en)(yn)ylene includes lower alk(en)(yn)ylene. There may be optionally inserted along the alkynylene group one or more oxygen, sulfur or substituted or unsubstituted nitrogen atoms, where the nitrogen substituent is alkyl. Alk(en)(yn)ylene groups include, but are not limited to, —C=C—(CH$_2$)$_n$—C≡C—, where n is 1 or 2. The term "lower alk(en)(yn) ylene" refers to alk(en)(yn)ylene groups having up to 6 (e.g., 1, 2, 3, 4, 5, or 6) carbons. In certain embodiments, alk(en)(yn)ylene groups have about 4 (e.g., 1, 2, 3, or 4) carbon atoms.

As used herein, "cycloalkylene" refers to a divalent saturated mono- or multicyclic ring system, in certain embodiments of 3 to 10 (e.g., 3, 4, 5, 6, 7, 8, 9, or 10; 3-5, 3-6, 3-10, or 6-10) carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 (e.g., 5, 6, 7, 8, 9, 10, 11, 12, 13, 14, or 15; 5-8, 5-10, 8-12, or 10-15) atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from Q1.

As used herein, isothiocyanate (ITC) refers to a —N═C═S moiety.

Where the number of any given substituent is not specified (e.g., haloalkyl), there may be one or more substituents present. For example, "haloalkyl" may include one or more of the same or different halogens.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

The Compositions of Matter

The compositions provided herein for use in the pharmaceutical compositions and methods provided herein exhibit in vitro and in vivo activity against microbial diseases and infections. In one embodiment, the compounds treat or ameliorate one or more symptoms associated with a microbial disease or infection. In a related embodiment, the compounds affect the growth of bacteria. In another related embodiment, the compounds affect the growth of a fungus. In yet another related embodiment, the compounds of the present invention inhibit protozoal growth. The compositions provided herein for use in the pharmaceutical compositions and the methods provided herein also exhibit in vitro activity against a cancer.

In one embodiment, the compositions for use in the compositions and methods provided herein have formula I:

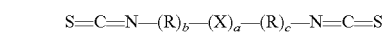

where a, b, and c are independently 0 or 1, provided that a, b, and c are not all 0;

X is an aryl or heteroaryl ring system which may be unsubstituted or substituted with from 1 to 4 moieties selected from —Br, —Cl, —OH, —NH$_2$, —COOH, OR'—CH$_3$ or R"—CH$_3$ wherein R' and R", independently, are an alkylene moiety having the formula —(CH$_2$)$_n$—, where n can be an integer from 0 to 20 (e.g., 0, 1, 2, 3, 4, 5, 6, 7, 8, 9, 10, 11, 12, 13, 14, 15, 16, 17, 18, 19, or 20); and each R, independently, is selected from the group consisting of linear or branched alkylene, alkenylene, and alkynylene moieties having from 1 to 20 C atoms; linear or branched heteroalkylene moieties having from 2 to 20 C (e.g., 2, 3, 4, 5, 6, 7, 8, 9, 10, 11, 12, 13, 14, 15, 16, 17, 18, 19, or 20) atoms and from 1 to 3 (e.g., 1, 2, or 3) O, N or S atoms; and arylene, heteroarylene, and cycloalkylene moieties having from 5 to 10 C atoms (e.g., 5, 6, 7, 8, 9, or 10) and from 1 to 3 (e.g., 1, 2, or 3) N, S, or O atoms.

In one embodiment, the compositions have formula I where X is a phenyl ring, a biphenyl ring, a napthyl ring, an anthrocyl ring, an indole ring, a pyrimidine ring, a pyrene ring, a furan ring, or a pyridine ring.

In another embodiment, the compositions have formula I where a and b are 0, c is 1. In another embodiment, the compositions have formula I where R, independently, is an alkylene moiety having the formula —(CH$_2$)$_n$—, where n can be an integer from 1 to 20. In some embodiments, n is 4, 5, 6, 7, 8, or 9.

In another embodiment, compositions having formula I, and where X is a phenyl ring, have R, independently, as an alkylene moiety having the formula —(CH$_2$)—.

In related embodiments, compounds having formula I, and where X is a phenyl ring and c is 0, a and b are 1, have R as an alkylene moiety having the formula —(CH$_2$)—.

In another embodiment, compounds having formula I and where a and b are 0, c is 1, have an R, independently, as an heteroalkylene moiety having the formula

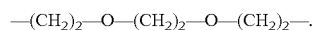

In another embodiment, the compounds of formula I have the chemical formula of compounds 16, 37, 38, 39, 40, 41, 42, or 43 of Table 1.

In another embodiment, the compositions for use in the pharmaceutical compositions and methods provided herein have formula II:

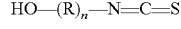

where R is an alkylene group having the formula —(CH$_2$)—, and n is an integer from 7-20 (e.g., 7, 8, 9, 10, 11, 12, 13, 14, 15, 16, 17, 18, 19, or 20).

In one embodiment, the compositions of formula II can have an n value of 7 or 8.

In another embodiment, the compositions of formula II have the chemical formula of compound 44 or 45 of Table 1.

In another embodiment, the compositions for use in the pharmaceutical compositions and methods provided herein have formula III:

where X is a pyrimidine ring where R is conjugated to the pyrimidine ring at any position 2-6 in the ring, and wherein the pyrimidine ring may be further substituted at any position with one or more moieties selected from —Br, —Cl, —OH, —NH$_2$, —COOH, OR'—CH$_3$ or R"—CH$_3$ wherein R' and R", independently, are an alkylene moiety having the formula —(CH$_2$)$_{n'}$— where n' can be an integer from 0 to 20 (e.g., 0, 1, 2, 3, 4, 5, 6, 7, 8, 9, 10, 11, 12, 13, 14, 15, 16, 17, 18, 19, or 20); and wherein R is selected from the group consisting of linear or branched alkylene, alkenylene, and alkynylene moieties having from 1 to 20 C atoms (e.g., 1, 2, 3, 4, 5, 6, 7, 8, 9, 10, 11, 12, 13, 14, 15, 16, 17, 18, 19, or 20); linear or branched heteroalkylene moieties having from 2 to 20 (e.g., 2, 3, 4, 5, 6, 7, 8, 9, 10, 11, 12, 13, 14, 15, 16, 17, 18, 19, or 20) C atoms and from 1 to 3 (e.g., 1, 2, or 3) O, N or S atoms; and arylene, heteroarylene, and cycloalkylene moieties having from 5 to 10 (e.g., 5, 6, 7, 8, 9, or 10) C atoms and from 1 to 3 (e.g., 1, 2, or 3) N, S, or O atoms.

In another embodiment, the compositions have the formula III where the R can be at position 2 or 3 of the pyrimidine ring.

In another embodiment, the compositions have the formula III where R is an alkylene moiety having the formula —CH$_2$—, and n is 1. In another embodiment, the R is heteroalkylene moiety having the formula —CH$_2$—O—CH$_2$—, and n is 1.

In certain embodiments, the compositions of formula III have the chemical formula of compounds 30, 31, or 32 of Table 1.

In another embodiment, the compositions for use in the pharmaceutical compositions and methods provided herein have the formula IV:

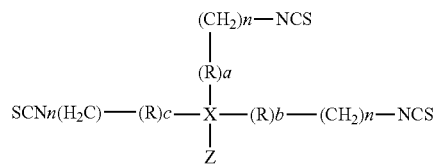

wherein X can be C, N, or P, provided that if X is N or P, Z is not present;

each n can range independently from 0 to 20 (e.g., 0, 1, 2, 3, 4, 5, 6, 7, 8, 9, 10, 11, 12, 13, 14, 15, 16, 17, 18, 19, or 20);

a, b, and c can be independently 0 or 1, provided that if a, b, or c is 0, then the n of the adjacent —(CH$_2$)$_n$— moiety is not 0;

each R can be independently selected from the group consisting of alkylene, heteroalkylene, arylene, heteroarylene, and cycloalkylene moieties having from 5 to 10 (e.g., 5, 6, 7, 8, 9, or 10) C atoms and from 1 to 3 (e.g., 1, 2, or 3) N, S, or O atoms; and Z can be selected from —Br, —Cl, —OH, —NH$_2$, —COOH, OR'—CH$_3$ or R"—CH$_3$ wherein R' and R", independently, are an alkylene moiety having the formula —(CH$_2$)$_{n'}$—, where n' can be an integer from 0 to 20 (e.g., 0, 1, 2, 3, 4, 5, 6, 7, 8, 9, 10, 11, 12, 13, 14, 15, 16, 17, 18, 19, or 20), and (CH$_2$)$_m$—NCS, where m can range from 1 to 20 (e.g., 1, 2, 3, 4, 5, 6, 7, 8, 9, 10, 11, 12, 13, 14, 15, 16, 17, 18, 19, or 20).

In one embodiment, the compositions have formula IV where X is a N, P, or C atom. In another embodiment, the compositions have formula IV where a, b, and c are 1, and R is a phenyl moiety.

In another embodiment, the compositions have formula IV a, b, and c are 0. In related embodiments, the compositions have formula IV where a, b, and c are 0, and Z has the chemical formula —(CH$_2$)$_m$—N=C=S.

In another embodiment, the compositions for use in the pharmaceutical compositions and methods provided herein have the formula V:

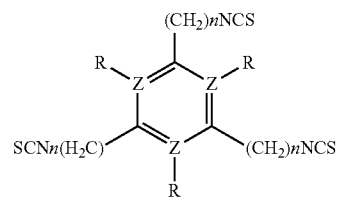

where each Z, independently, is C or N;

each R, independently, is selected from —H and —Br, —Cl, —OH, —NH$_2$, —COOH, OR'—CH$_3$ or R"—CH$_3$ wherein R' and R", independently, are an alkylene moiety having the formula —(CH$_2$)$_{n'}$—, where n' can be an integer from 0 to 20 (e.g., 0, 1, 2, 3, 4, 5, 6, 7, 8, 9, 10, 11, 12, 13, 14, 15, 16, 17, 18, 19, or 20); and each n can range independently from 0 to 20 (e.g., 0, 1, 2, 3, 4, 5, 6, 7, 8, 9, 10, 11, 12, 13, 14, 15, 16, 17, 18, 19, or 20).

In another embodiment, the composition has formula V where Z is N or C. In another embodiment R is H. In some embodiments, the composition has formula V where Z is N and R is H.

In another embodiment, the compositions for use in the pharmaceutical compositions and methods provided herein have the formula VI:

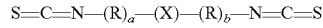

where a and b can be independently 0 or 1;

X can be an S, thionyl, or sulfuryl moiety; and and each R, independently, is selected from —H and —Br, —Cl, —OH, —NH$_2$, —COOH, OR'—CH$_3$ or R"—CH$_3$ wherein R' and R", independently, are an alkylene moiety having the formula —(CH$_2$)$_{n'}$— where n' can be an integer from 0 to 20 (e.g., 0, 1, 2, 3, 4, 5, 6, 7, 8, 9, 10, 11, 12, 13, 14, 15, 16, 17, 18, 19, or 20); and each n can range independently from 0 to 20 (e.g., 0, 1, 2, 3, 4, 5, 6, 7, 8, 9, 10, 11, 12, 13, 14, 15, 16, 17, 18, 19, or 20).

In one embodiment, the compositions have formula VI where X is S, a thionyl, or a sulfuryl moiety.

In another embodiment, the compositions for use in the pharmaceutical compositions and methods provided herein have the formula VII:

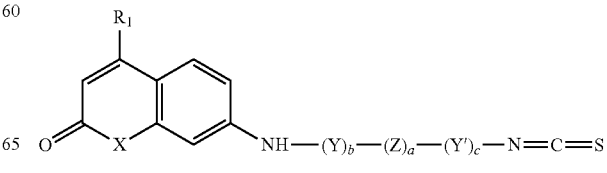

where a, b, and c are 1 or 0;

X is a C, O, or N atom;

Y or Y', independently, is a alkylene moiety having the formula (—CH$_2$)$_n$—, wherein n is an integer from 1 to 20 (e.g., 1, 2, 3, 4, 5, 6, 7, 8, 9, 10, 11, 12, 13, 14, 15, 16, 17, 18, 19, or 20);

Z is an aryl or heteroaryl ring system which may be unsubstituted or substituted with from 1 to 4 moeities selected from —Br, Cl, —F, —OH, —NH2, —COOH, —OR'—CH3, R"—CH3, wherein R' and R", independently, are an alkylene moiety having the formula —(CH$_2$)$_n$—, where n can be an integer from 0 to 20 (e.g., 0, 1, 2, 3, 4, 5, 6, 7, 8, 9, 10, 11, 12, 13, 14, 15, 16, 17, 18, 19, or 20);

each of R$_1$ is an H, NH; a linear or branched alkylene moiety having from 1 to 20 (e.g., 1, 2, 3, 4, 5, 6, 7, 8, 9, 10, 11, 12, 13, 14, 15, 16, 17, 18, 19, or 20) C atoms, and can be substituted with 1 to 3 (e.g., 1, 2, or 3) halo moieties; or a linear or branched heteroalkylene moiety having from 1 to 3 (e.g., 1, 2, or 3) N atoms, 1 to 20 (e.g., 1, 2, 3, 4, 5, 6, 7, 8, 9, 10, 11, 12, 13, 14, 15, 16, 17, 18, 19, or 20) C atoms, and 1 to 4 (e.g., 1, 2, 3, or 4) O atoms.

In one embodiment, the compositions have formula VII where X is C, O, or N. In another embodiment, the compositions have formula VII where X is O. In another embodiment, the compositions have formula VII where X is N. In another embodiment, the compositions have formula VII where R$_1$ is CH$_3$. In another embodiment, compositions have formula VII where a, b, and c are 1. In another embodiment, compositions have formula VII where a and b are 0, and c is 1.

In another embodiment, the compositions have formula VII where Y and Y' or Y and Y' independently are alkylene moieities having the formula —(CH$_2$)—.

In another embodiment, the compositions have formula VII where Z is a phenyl ring. In another embodiment, the compositions have formula VII where Y' is a linear alkylene moiety having the formula —(CH$_2$)$_n$—. In certain embodiments, the compositions having formula VII where Y' is a linear alkylene moiety having the formula —(CH$_2$)$_n$—, n is 6.

In another embodiment, the compositions have formula VII and R$_1$ is —CF$_3$. In another embodiment, the compositions have formula VII where X is N and R$_1$ is —CF$_3$. In certain embodiments, the compositions have formula VII and have the chemical structure of compounds 59, 67, 68, or 69 of FIG. 6.

Preparation of the Compounds

The compositions for use in the pharmaceutical compositions and methods provided herein may be prepared by methods well known to those of skill in the art, or by the methods shown herein. One of skill in the art would be able to prepare all of the compounds for use herein by routine modification of these methods using the appropriate starting materials.

Such methods for making the compositions provided herein are provided in the Examples section (see Example I).

Additional compositions provided herein may be made by the synthetic routes shown below. For example, certain tri- and multi-functional ITC compounds were made using the synthetic route shown below.

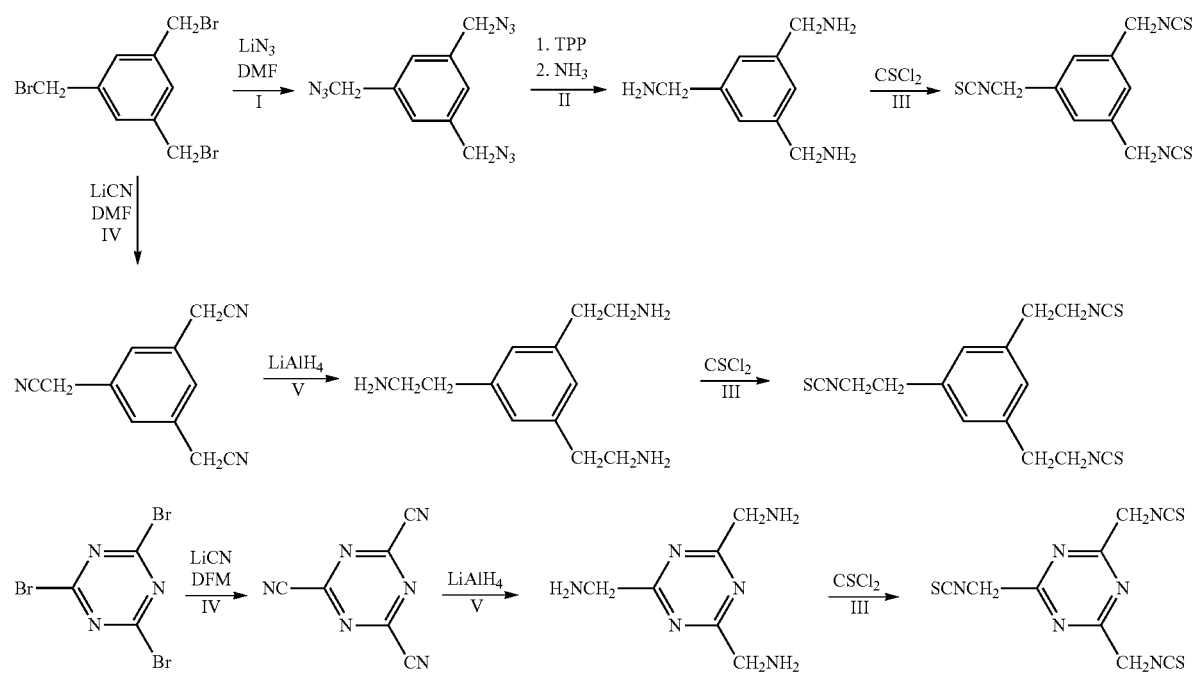

Figure 5:
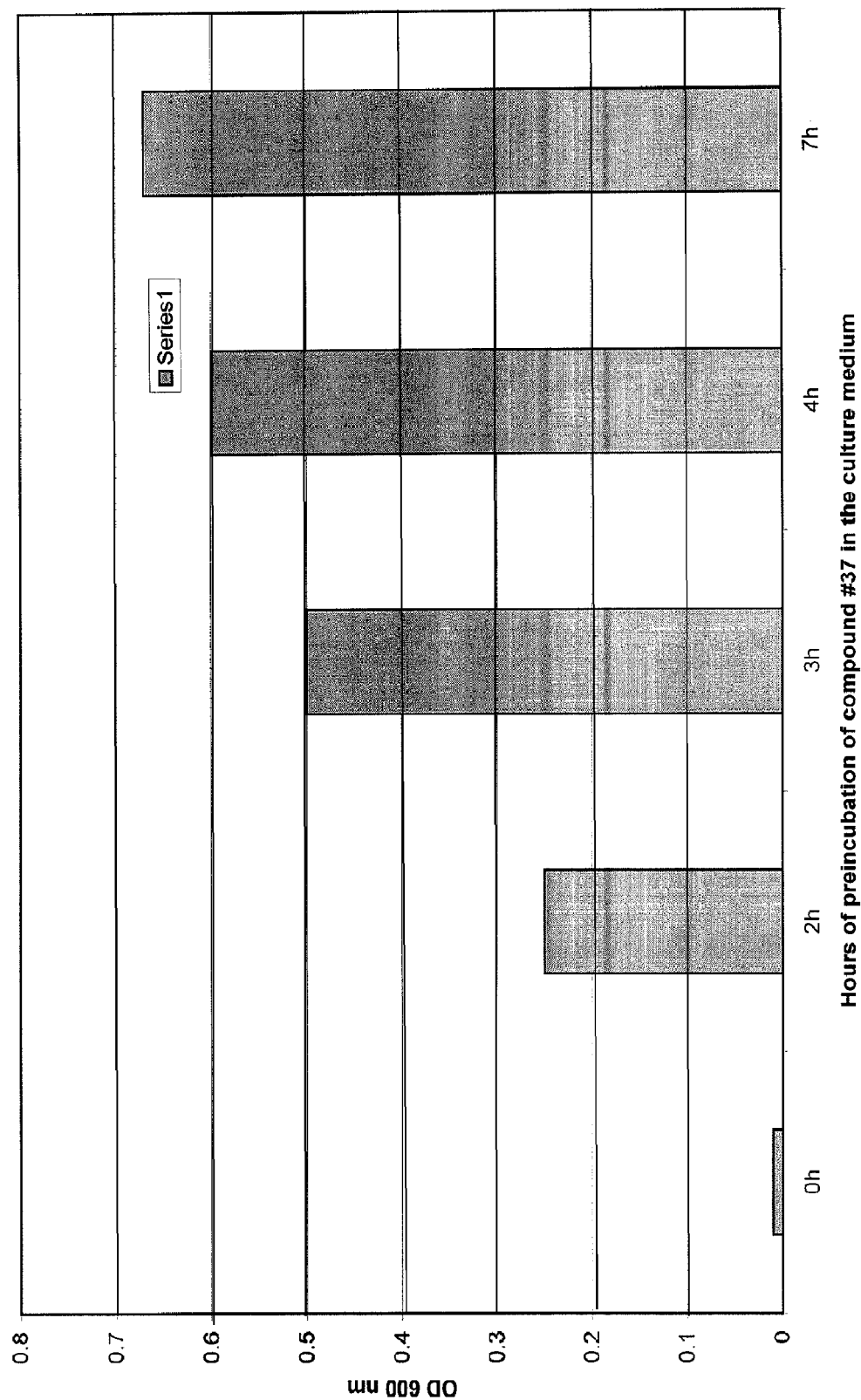
FIG. 5 is a bar graph depicting the effect of pre-incubation of compound 37 in the culture media on its inhibitory potency towards *Bacillus cereus*. The X-axis represents the time in hours of preincubation of Compound 37 in growth media. The Y-axis represents the relative Minimum Inhibitory Concentration (MIC) reported in ug/mL.

The chemical reactions used in this scheme are similar to those described in the protocols below (see, Example I). Thus, the immediately above reaction steps I, II, III can be performed as for the synthesis of compound 59 of FIG. 5, or as for homologs of compound 45 of Table 1. Reaction IV is an alkylation of the cyanide nucleophile. This method can be performed in DMF using either lithium cyanide or cupric cyanide. Reaction V is reduction of the nitrile compound, and can be accomplished by using lithium alumohydride or borane-tetrahydrofurane complex.

Other compounds provided herein can be prepared by the scheme shown below:

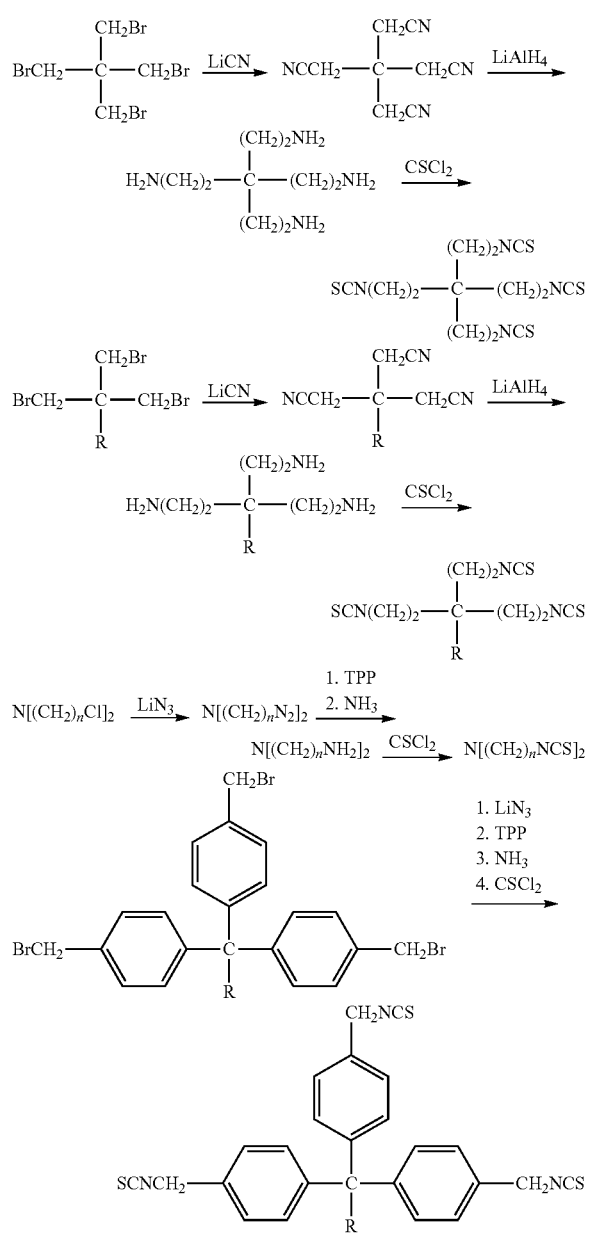

Such synthetic reactions are the same as described below in the Examples (see, Example I), and can be performed by the disclosed protocols. How to optimize the reaction conditions for a particular compound is well known to one of ordinary skill in the art, and can include, for example, variation of the incubation conditions (temperature, incubation time, etc.) or purification methods.

Formulation of Pharmaceutical Compositions

The pharmaceutical compositions provided herein contain one or more of the compounds provided herein that are useful in the treatment of or amelioration of one or more of the symptoms of a microbial diseases or infection. Microbial infections can be caused by microbial pathogens, such as, bacteria, fungi, or protozoa. The pharmaceutical compositions provided herein contain one or more of the compounds provided herein that are useful in the treatment of cancer. Pharmaceutical carriers suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats or ameliorates the symptoms of microbial infection/disease or that treats a cancer.

In one embodiment, the compositions are formulated for single dosage administration. To formulate a composition, the weight fraction of compound is dissolved, suspended, dispersed or otherwise mixed in a selected carrier at an effective concentration such that the treated condition is relieved or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein (see, e.g., Example 2, Example 8).

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to treat or ameliorate a microbial infection.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Also provided by the invention are compositions for use in treating dental caries or tooth decay. Examples of useful oral carriers for delivering the compositions to the mouth include, but are not limited to, tooth pastes, chewing gums, lozenges, topical ointments or creams, mouth washes, coated dental floss or tape, and mouth rinses.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

In additional embodiments, the solid formulations can be a chewing gum, a lozenge, a toothpaste, or topical cream or ointment.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Additional acceptable liquid-phase carriers for oral delivery include, for example, mouth washes or mouth rinses.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

General Dosages and Toxicity

The dose will be determined by the efficacy of the particular compound employed and the condition of the subject, as well as the body weight or surface area of the subject to be treated. The size of the dose also will be determined by the existence, nature, and extent of any adverse side effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. Many different administration methods are known to those of skill in the art.

For administration, compounds of the present invention can be administered at a rate determined by factors that can include, but are not limited to, the pharmacokinetic profile of the compound, contraindicated drugs, and the side effects of the compound at various concentrations, as applied to the mass and overall health of the subject. Administration can be accomplished via single or divided doses.

Toxicity and therapeutic efficacy of such compounds can be determined known pharmaceutical procedures in cell cultures or experimental animals (animal models of infection, e.g., tuberculosis, or animal cancer models, e.g., colon, breast, prostate, or lung cancer models). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating an infection or cancer in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

It is furthermore understood that appropriate doses of a small molecule depend upon the potency of the small molecule with respect to the inhibition of the cell growth (i.e., inhibition of the growth of a microbial or cancer cell). When one or more of these small molecules is to be administered to an animal (e.g., a human) to treat an infection or a cancer, a physician, veterinarian, or researcher may, for example, prescribe a relatively low dose at first, subsequently increasing the dose until an appropriate response is obtained.

Articles of Manufacture

The compounds or pharmaceutically acceptable derivatives may be packaged as articles of manufacture containing packaging material, a compound or pharmaceutically acceptable derivative thereof provided herein, which is effective for treatment or amelioration of one or more symptoms of a microbial infection/disease or in the treatment of a cancer, within the packaging material, and a label that indicates that the compound or composition, or pharmaceutically acceptable derivative thereof, is used for treatment or amelioration of one or more symptoms of a microbial infection/disease or in the treatment of a cancer.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any microbial infection/disease or cancers.

Sustained Release Formulations

Also provided are sustained release formulations to deliver the compounds to the desired target (i.e. brain or systemic organs) at high circulating levels (between $10^{-9}$ and $10^{-4}$ M). It is understood that the compound levels are maintained over a certain period of time as is desired and can be easily determined by one skilled in the art. In one embodiment, the administration of a sustained release formulation is effected so that a constant level of therapeutic compound is maintained between $10^{-8}$ and $10^{-6}$ M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, in one embodiment 20 to 25%, and the amount of coating will be from 10 to 25% of the weight of the active material, and in another embodiment, 15 to 20% of the weight of active material. Any conventional pharmaceutically acceptable plasticizer may be incorporated into the coating.

The compounds provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the active compound. In one embodiment, the compounds are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

Combination Therapy

The compounds and compositions provided herein may also be used in combination with other active ingredients. In another embodiment, the compounds may be administered in combination, or sequentially, with another therapeutic agent. Such other therapeutic agents include those known for treatment or amelioration of one or more symptoms of a bacterial infection. Such therapeutic agents include, but are not limited to, ampicillin, amoxicillin, co-amoxiclav, flucolaxacillin, cefalexin, cefaclor, cefuroxime, tetracycline, doxycycline, oxytetracycline, gentamicin, neomycin, erythromycin, clarithromycin, ciprofloxacin, vancomycin, trimethoprim, clindamycin, chloramphenicol, isoniazid, metronidazole, and rifampacin.

In another embodiment, such other therapeutic agents include those known for treatment or amelioration of one or more symptoms of a fungal infection. Such therapeutic agents include, but are not limited to, amorolfine, butenafine, naftifine, terbinafine, flucytosine, fluconazone, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, primaricin, griseofulvin, ciclopirox, haloprogin, tolnaftate, and undecylenate.

In another embodiment, such other therapeutic agents include those known for treatment or amelioration of one or more symptoms of a protazoan infection. Such therapeutic agents include, but are not limited to, metronidazole, eflornithine, furazolidone, hydroxychloroquine, iodoquinol, and pentamidine.

In yet another embodiment, such other therapeutic agents include those known for treatment or amelioration of one or more symptoms of a cancer. Such therapeutic agents include, but are not limited to, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-flurouracil, vincristin, vinblastin, methotrexate, Herceptin, and an analog of any of the aforementioned.

Dental Formulations and Applications Thereof

Dental Formulations

Provided herein are compositions including anti-microbial compounds useful in the treatment of a microbial disease or infection. Particularly featured herein are compositions for the prophylactic and therapeutic treatment of microbial dental caries and microbial periodontal disease. Periodontal disease also encompasses dental plaque. The composition can be delivered to the teeth, the gums, or the mouth of a subject, and depending on, for example, the location where the composition is to be applied, the composition can be formulated as a solid (e.g., a gel, a paste, a powder, an ointment, a lotion, a lozenge), a liquid, or a suspension (e.g., a mouth wash, a mouth rinse, a slurry).

The composition for treating and/or preventing periodontal disease according to the present invention may be one simply containing any of the compositions described herein as an effective component, but the antimicrobial activity thereof can further be improved by the use of an appropriate additional components, such as, an organic acid. Examples of such organic acids are malic acid, citric acid, lactic acid, oxalic acid, malonic acid, succinic acid, fumaric acid, acetic acid, benzoic acid, phenylacetic acid, salicylic acid and phenols.

The amount of the organic acid to be used preferably ranges from 0.01 to 5% by mass, more preferably 0.02 to 3% by mass and most preferably 0.05 to 1.5% by mass on the basis of the total mass of the composition for treating and/or preventing periodontal disease.

The composition for the treatment and/or prevention of the periodontal disease according to the present invention may comprise only a composition described herein or the combination of the composition and an organic acid, or the resulting composition may further admixed with other components and/or a carrier. The dosage forms of the composition for the treatment and/or prevention of the periodontal disease may be liquid, solid or gaseous ones. The composition for the treatment and/or prevention of the periodontal disease may be administered through either the oral route or any parenteral route. Examples of the dosage forms of the composition are a powdery preparation, a liquid preparation (e.g., a mouth wash), a chewing gum, a paste, a lozenge, a jelly, a cream, an ointment, a butter, or in some aspects, various forms of foods such as a candy or starch jelly. In some instances, the compositions can be administered locally to an affected area of the mouth. Dosage forms for local administration of the compositions include, but are not limited to, coated or otherwise coupled to solid matrices, such as dental floss, dental tapes, gauze, or a tooth brush for direct application to an affected area (e.g., a site of dental caries).

Among these dosage forms, those for the local administration such as a cream, paste, and an ointment are preferably used since they are suitable for the direct application to an affected part suffering from the periodontal disease or a decayed tooth.

In the preparation of the composition for the treatment and/or prevention of the dental caries or periodontal disease, in a variety of dosage forms, there may be used, for instance, a base component such as an oily component, a humectant and/or an antiseptic, which are commonly used in pharmaceutical compositions, cosmetic products, compositions applied to the skin and compositions intra-orally administered (such as a tooth paste and a mouth wash). The compositions also can include a flavoring agent which masks the flavor of various components of the compositions (e.g., detergent component or active ingredient). Examples of flavoring agents include, spearmint, cinnamon, wintergreen, and menthol, fennel. Mint flavors can be especially useful when combined with menthol, which contain oils that volatilize in the warmth of the mouth.

Water used in the composition for the prevention and/or treatment of the periodontal disease are not restricted to particular ones and examples thereof include tap water, natural water and purified water, but preferably used herein is highly purified water such as ion-exchange water.

Examples of oily components usable herein are oils derived from animals such as squalane, tallow, lard, horse fat, lanolin and beeswax; oils derived from vegetables such as olive oil, grape seed oil, palm oil, jojoba oil and germ oil (such as rice germ oil); and synthetic or semi-synthetic oils such as liquid paraffin, higher fatty acid esters (such as octyl palmitate, isopropyl palmitate and octyl dodecyl myristate) and silicone oil.

The oily components are used in appropriate combinations while taking into consideration the performance requirement, for instance, an ability of protecting the skin (i.e., lips) or the soft tissue of the cheek or gums, an effect of imparting emollient (or an effect of preventing drying of the skin and imparting softness and resilience to the skin through the coverage of the skin surface with a thin film) and an ability of imparting refreshed feeling to the skin. In one of preferred examples of such combinations, the oily component comprises squalane, olive oil and octyl dodecyl myristate.

The composition for the treatment and/or prevention of the periodontal disease comprises a solid oil component such as stearic acid, stearyl alcohol, behenic acid, cetanol and vaseline to control the hardness and flowability of the resulting composition and the composition preferably comprises stearic acid and cetanol in combination.

Cream formulations of the present compositions can be generated using a creaming agent. Such creaming agents include, but are not limited to, glycerin monostearate and/or a self-emulsifiable glycerin monostearate (a product obtained by incorporating an emulsifying agent into glycerin monostearate), which can be used together.

Moreover, the composition for the treatment and/or prevention of the periodontal disease according to the present invention may, if necessary, comprise other additives such as a stabilizer, a humectant (a wetting agent), a wound-healing agent, an antiseptic, a surfactant, a binder, a foaming agent, a sweetening agent, a refrigerant and/or an abrasive.

Examples of stabilizers are a combination of a carboxy vinyl polymer with potassium hydroxide; polyethylene glycol distearate; and magnesium phosphate. In particular, polyethylene glycol sesqui-stearate (a 1:1 mixture of polyethylene glycol distearate and polyethylene glycol monostearate) (the molecular weight of the polyethylene glycol ranging from 1000 to 20,000) is preferably used herein since it has high stability, is not separated into water and oil and the hardness required when the composition is applied to the skin in the form of a cream composition can effectively be controlled. Examples of humectants (wetting agents) usable herein are sodium salt of hyaluronic acid, collagen, an aloe extract (in particular, the aloe extract (2) derived from Aloe arborescens is preferred), urea, 1,3-butylene glycol, glycerin, trehalose, sorbitol, amino acids and sodium salt of pyrrolidone carboxylic acid. Examples of wound-healing agents usable herein are allantoin, di-potassium glycyrrhizinate, a glycyrrhiza extract and a mugwort extract. The antiseptic is used subsidiarily since the compositions of the present invention have antibiotic effect by nature. Examples of such antiseptics are sodium benzoate, lower alkyl esters of p-hydroxy benzoic acid (for instance, so-called paraben such as methyl, ethyl, propyl or butyl ester), sodium propionate, mixed fatty acid esters (a mixture of capric acid glyceryl, lauric acid glyceryl-2 and lauric acid polyglyceryl-10), phenoxy ethanol, light-sensitive substance No. 201 (yellow dye), and 1,2-pentanediol. Examples of the foregoing surfactants are sodium N-acyl-L-glutamate and polyoxyethylene sorbitan monostearate. Examples of the binders usable herein include sodium carboxymethyl cellulose; examples of the foaming agents are sodium lauryl sulfate, sodium lauroyl glutamate, and sodium lauroyl sarcosinate; examples of the sweetening agents are xylitol, sorbitol and saccharin sodium; examples of the refrigerants include mint essence; and examples of the abrasives are calcium phosphate, calcium hydrogen phosphate and silica.

Application of the Dental Compositions

It is desirable to apply the composition for the treatment and/or prevention of the periodontal disease to the affected part, such as the affected part of the mouth with periodontal disease (e.g., caries, or plaque formation), such as the tooth root of a decayed tooth or the periodontium. This will workably be applied in an appropriate amount on the order of, for instance, 0.1 to 1 g, at a frequency ranging from 1 to 5 times, usually 1 to 3 times a day, when it is used in the form of a cream composition. It can also be given as one or more than one lozenge daily, or one or more than one daily wash or rinse with any of the oral liquid formulations discussed above. The amount and frequency of application of the composition may appropriately be changed while taking into consideration, for instance, the symptoms of the disease, the microbial agent causing the disease, the extent of disease, and the subject to be treated. When the composition is a paste or gel, it can be applied by means, for example, of a toothbrush one or more than one times daily as dictated by symptoms and recommended by physician.

The composition for the treatment and/or prevention of the periodontal disease is desirably taken in an appropriate amount on the order of, for instance, 0.01 to 0.1 g/1 kg of body weight at a frequency ranging from 1 to 5 times, usually 1 to 3 times a day, when it is administered through a parenteral route (e.g., non-enteral or mucosal routes, e.g., injection, topical).

Compositions for, and Methods of, Food Preservation

Disclosed herein is a food preservative composition which includes at least one of any of the compositions of matter described herein. Provided herein is a composition for preserving food by preventing the growth of a microbial food contaminant (e.g., bacteria, fungus, or protozoa) by contacting the food with an effective amount of at least one of any of the chemical compositions claimed herein. In some aspects, the composition can be a solution. The composition can further comprise a carrier, e.g., water. The composition can further comprise a surfactant (e.g., alkyl glucoside) and water. The composition may be a solution of a chemical composition claimed herein and water.

The compositions can further comprise a flavoring agent, for example, citral, pinene, nerol, b-ionone, geraniol, carvacrol, eugenol, carvone, terpeniol, anethole, camphor, menthol, limonene, nerolidol, farnesol, phytol, carotene (vitamin $A_1$), squalene, thymol, tocotrienol, perillyl alcohol, borneol, myrcene, simene, carene, terpenene, linalool, or mixtures thereof.

The food preservative composition is effective against various infective microbes including bacteria, protozoa, and/or fungi.

Application

A method for preserving food is disclosed. The method includes contacting a food product with one or more of any one of the compositions described herein.

The method of contacting the food can comprise, for example, spraying, dipping, soaking, or impregnating food with the food preservative compositions described herein.

The application of the method can be by spraying on unspoiled food a solution containing a claimed chemical composition with or without water or a surfactant.

The invention provides preservation for all types of food utilized for human or animal consumption by the addition of any one or more than one of the chemical compositions claimed herein with biocidal (e.g., anti-microbial) activity.

Wood Preserving Compositions and Application Thereof

The present invention also provides wood preserving compositions which include one or more than one of the chemical compositions claimed herein. The compositions are particularly useful in inhibiting the growth of a microbe growing on, near, or within a wood. Microbes, or microbial pests that contribute to the decay or deterioration of a wood, inhibited by the wood preserving compositions of the invention include, but are not limited to, fungi and bacteria. The invention also features methods of preserving wood by contacting the wood with the wood preserving compositions.

Compositions

The compositions useful in preserving wood can contain one or more than one of the chemical compositions claimed herein, and can also include additional performance-enhancing, non-biocidal, products such as water repellants, colorants, emulsifying agents, dispersants, stabilizers, UV inhibitors, drying agents, polymer systems and the like disclosed herein to further enhance the performance of the system or the appearance and performance of the resulting treated products.

These include a wide range of organic carriers. Non-limiting examples of organic carriers that can be used, either alone, or as mixtures, as solubility allows, include:

Amines such as, for example: Diamylamine, Diethylamine, Diisopropylamine, Dimethylethylamine, Di-n-Butylamine, Mono-2-Ethylhexyamine, Monoamylamine, Monoethylamine 70%, Monoisopropylamine, Anhy., Mono-n-Butylamine, Triamylamine, Triethylamine, Tri-n-Butylamine, Dibutylaminoethanol, Diethylaminoethanol, Diethylaminoethoxyethanol, Diisopropylaminoethanol, Dimethylamino-2P, 77% Mixed, Dimethylamino-2-P, Anhy., Dimethylaminoethanol, Dimethylaminoethoxyethanol, Ethlylaminoethanol, Ethylaminoethanol, Mixed, Isopropylaminoethanol, Isopropylaminoethanol, Mixed, Methyldiethanolamine, Monomethylaminoethanol, Mono-n-Propylaminoethanol, n-Butylaminoethanol, n-Butyldiethanolamine, n-Butyldiethanolamine, Photo, t-Butylaminoethanol, t-butyldiethanolamine, Diethanolamine, Monoethanolamine, Triethanolamine, Triethanolamine 85%/99%, Diisopropanolamine, Monoisopropanolamine, Triisopropanolamine, Aminoethylethanolamine, Aminoethylpiperazine, Diethylenetriamine, Ethylenediamine, Piperazine 65%/Anhy., Piperazine, Tetraethylenepentamine, Triethylenetetramine, 3-Methoxypropylamine. Regular/95, Cyclohexylamine, Morpholine, Glycols, such as, for example: Diethylene Glycol, Dipropylene Glycol, Ethylene Glycol, Glycerine 96%, 99%, U.S.P., Glycerine, Hexylene Glycol. Neopentyiglycol, Polyethylene Glycol, Polypropylene Glycol, Propylene Glycol Ind.,U.S.P., Tetraethylene Glycol, Triethylene Glycol, Tripropylene Glycol; Ketones such as, for example: Acetone, Cyclohexanone, Diacetone, DIBK-Diisobutyl Ketone, Isophorone, MAK-Methyl Amyl Ketone, MEK-Methyl Ethyl Ketone, MIAK-Methyl Isoamyl Ketone, MIBK-Methyl Isobutyl Ketone, MPK-Methyl Propyl Ketone; Esters such as, for example: Amyl Acetate, Dibasic Ester, Ethyl Acetate, 2 Ethyl Hexyl Acetate, Ethyl Propionate. Acetate Esters, Isobutyl Acetate, Isobutyl Isobuterate, Isopropyl Acetate, n-Butyl Acetate, n-Butyl Propionate, n-Pentyl Propionate, n-Propyl Acetate; Alcohols such as, for example: Amyl Alcohol, Benzyl Alcohol, Cyclohexanol, Ethyl Alcohol-Denatured, 2-Ethyl Hexanol. Isooctyl Alcohol, Isodecyl Alcohol. Tridecyl Alcohol, Furfuryl Alcohol, Isobutyl Alcohol, Isopropyl Alcohol 99% Anhy, Methanol, Methyl Amyl Alcohol (MIBC), n-Butyl Alcohol, n-Propyl Alcohol. Linear Alcohol, Secondary Butyl Alcohol, Tertiary Butyl Alcohol, Tetrahydrofurfryl Alcohol.

Halogenated carriers include, for example: Methylene Chloride, Monochlorobenzene, Orthodichlorobenzene, Perchloroethylene, Trichloroethylene, Hydrofluorocarbon; Aliphatic Carriers such as, for example: Heptane, Hexane, Kerosene, Lacquer Diluent, Mineral Seal Oil, Mineral Spirits, n-Pentane, OMS-Odorless Mineral Spirits, Rubber Solvent, 140 Solvent, 360 Solvent, VM&P; Aromatic Carriers such as, for example: Aromatic 100, Aromatic 150, Aromatic 200, Heavy Aromatic Solvent, Toluene, Xylene; Other carriers, including, for example: mineral oil, linseed oil, olive oil, vegetable oil, methoxypropyl acetate, isopropyl alcohol, castor oil, Propylene Carbonate, #2 fuel oil, Cycloparaffin Solvent, DMF—dimethyl formamide, formamide, Ink Oil/Solvent, furfural. Isoparaffin Solvent, MTBE—methyl tert-butyl ether, NMP—N-methyl pyrrolidone, Normal Paraffin Solvent, Glycol Diether, THF—tetrahydrofuran. Aliphatic Solvent.

Application of Wood Preservative Compositions

In one aspect, the invention is a method of wood preservation comprising treating the wood with at least one of the compositions of the invention. One of ordinary skill in the art will understand that such treatments will vary, for example, according to the type or size of wood, the type of infection of the wood, the extent of the infection or infestation of the wood, or the environmental conditions the wood is exposed to. Workable treatment strategies for a wood can include, for example, treatment for a few minutes, a few hours, or a few days. The composition can be used at any concentration, including, but not limited to about 0.01 g/l, about 1.0 g/l, and about 100 g/l. In one embodiment, the wood is treated for two days at two atmospheres with 0.1 g/l of solids in water or other acceptable solvent, diluent, or carrier.

Wood preserving compositions disclosed herein can be applied (i.e., contacted, administered) to a wood by any means known to one of ordinary skill and can include, for example, surface treatment (e.g., topical application), pressure-treatment, fumigation, or impregnation of the wood.

Where the wood preserving compositions are a liquid or dissolved in a liquid form, the compositions can be applied to a wood by painting, spraying, dipping or soaking of the wood with the composition or compositions. Where the wood preserving composition is a vapor, aerosol, or a liquid, the composition can be applied to a wood by fumigation technigues.

Where the wood preserving compositions disclosed herein are in solid form, the compositions can be applied to a wood, for example, by rubbing the solid onto the wood. The solid compositions can be particularly useful for inhibiting internal decay of a wood when internally applied to the wood (e.g., impregnated into the wood). Methods for inserting such treatments into a wood are well known to those of ordinary skill, and can for example, include incising, through boring, radial drilling, and kerfing (see, for example, Graham, R D. (1983) Proceedings American Wood Preserver's Association 79:222-228; Graham, R D. (1973) Holz-forschung 27(1):168-173; and Graham et al. (1979) Forest Research Laboratory Research Bulletin 24, OSU, Corvallis, Oreg. 64 p.).

Evaluation of the Activity of the Compositions
In Vitro Methods
Methods of Screening for Cell Growth Inhibition The present invention features a method of inhibiting the growth of a cell using compositions (e.g., compounds) having the formula I, II, III, IV, V, VI, or VII. The method involves contacting a cell with the composition, and can include the additional step of determining whether the composition inhibits the growth of the cell. Inhibition of cell growth can be either "static" or "cidal" inhibition. Compositions that display static inhibition of a cell are understood to be compositions that inhibit the growth of cell when present (i.e., in the cell culture medium, or otherwise in contact with the cell), but once removed, no longer inhibit the growth of a cell. Compositions that possess static growth inhibition activity on a cell are sometimes also called "reversible inhibitors" of cell growth. In contrast, a composition having the formula I, II, III, IV, V, VI, or VII, that demonstrates a "cidal" effect is understood to be a composition that can kill a cell that is contacted by the composition. Such cell killing can be, for example, through direct or indirect lysis of the cell, inhibition of a critical function of the cell (e.g., electron transport chain, ATP synthesis, sugar metabolism), or in the case of certain eukaryotic cells (e.g., nematode cells, fly cells, mammalian cells, mouse or human cells), induction of programmed cell death or apoptosis. One of skill in the art would understand that a cidal composition can also be referred to as an "irreversible inhibitor" of cell growth.

Cidal and static activities possessed by the claimed compositions are not mutually exclusive for a given composition, and for particular compositions having formula I, II, III, IV, V, VI, or VII, for example, Compound 37, may exhibit both static and cidal effects depending on the cell tested, the growth conditions (e.g., culture media, temperature, incubation time), and the concentration of the compound used in the test.

A cell which is inhibited by any composition of the present invention can be a prokaryotic cell (e.g., a bacterial cell, a protozoan cell) or a eukaryotic cell (e.g., a fungal cell, a yeast cell, a nematode cell, a mammalian cell, a mouse or human cell). The bacterial cell can be pathogenic or non-pathogenic. The pathogenic or non-pathogenic bacterial cell inhibited by a composition having formula I, II, III, IV, V, VI, or VII can be either gram negative or gram positive, and can include, for example, any bacteria from the following list: *Bacillus cereus, Bacillus subtilis, Staphylococcus epidermis, Staphylococcus aureus, Streptococcus pyogenes, Enterococcus faecium, Enterococcus faecalis, Mycobacterium tuberculosis, Mycobacterium avium, Mycobacterium bovis, Haemophilus ducreyi, Neisseria gonorrheae, Micrococcus luteus, Klebsiella pneumoniae, Psuedomanas aeruginosa*, or *Bacillus anthracis*. In additional embodiments, the microbial cell inhibited by a composition of the present invention can be a fungal cell. The fungal cell can be, for example, of a filamentous fungi, a yeast, or a tinea, or the cell can be a fungal cell selected from the list of: *Aspergillus fumigatus, Candida glabrata, Candida albicans, Candida glabrata, Candida crusei, Candida parapsilosis*, and *Cryptococcus neoformans*. The microbial cell inhibited by a composition having formula I, II, III, IV, V, VI, or VII can also be a protozoan cell. The protozoan cell can be, for example, any one of the protozoan species from the list comprising: *Endamoeba hartmanii, Dientamoeba fragilis, Giardia lamblia, Balantidium coli, Toxoplasma gondii, Giardia duodenalis, Entamoeba histolytica, Cryptosporidium parvum, Cyclospora cayetanensis, Isospora belli, Leishmania braziliensis, Leishmania tropica, Leishmania infantum* and *Leishmania amazonensis, Plasmodium vivax, Plasmodium ovale*, and *Microsporidia*. In an alternative embodiment, a cell whose growth can be inhibited by a composition having formula I, II, III, IV, V, VI, or VII can be a mammalian cell, for example, a human cancer cell. The cancer cell can be, for example, from a colon cancer, a breast cancer, a lung cancer, a prostate cancer, a bone cancer, or a liquid tissue cancer (i.e., a lymphoma or a leukemia). The cancer cell can be a clinical isolate obtained from a subject having the cancer, or can be a cell line (e.g., an immortalized cell line) generated in vitro using methods known to those of ordinary skill in the art.

Methods of determining whether cell growth is inhibited by an agent or a compound are well known to those of skill in the art. For bacteria, in some instances, the cells are seeded (e.g., grown or cultured) in 96 well plates (or flasks, bottles, dishes) at 37° C. in an appropriate growth medium (e.g., LB media, MHB media) at one concentration and exposed to serial dilutions of a test compound (e.g., a composition of formula I, II, III, IV, V, VI, or VII) ranging from, for example, 10 µM to 0.1 µM of the compound (e.g., 100 to 1 µM, 1 to 0.01 µM, 0.1 to 0.001 µM). Alternatively, the bacteria can also be serially diluted across the plate, for example, in 1 to 2, 1 to 5, or 1 to 10 dilutions across the 12 horizontal wells of a 96 well plate. In the case where the bacteria have been serially diluted across a given plate, one or more compounds can be used at 1 concentration for testing. Alternatively, bacteria grown at or to a single concentration in a plate can be exposed to serially diluted compounds (e.g., serially diluted down the vertical wells of the plate). In another method, both compound and bacteria can be diluted on a given plate such that different concentrations of a bacterial culture can be tested against different concentrations of a given compound. Often, a control compound (e.g., a known inhibitor of known concentration, or MIC value) is also added to a control set of cells as an internal standard. Often, a set of cells are grown in the presence of a carrier, buffer, or solvent (e.g., an alcohol, DMSO, PBS), in which the compound is delivered. Similar methods are employed for growing fungi and protozoa, and are well known to those of ordinary skill in the art (see, for example, Elledge et al. (1990) Genes Dev. 4(5):740-751; Navas et al. (1995) Cell 80(1):29-39; Lambros et al. (1979) 65(3):418-420; and Goldberg et al. (1997) 272(10):6567-6572). Methods of quantitating the inhibition of the microbial cell by a compound are discussed, for example, in Miyazawa et al. (2006) Biol. Pharm. Bull. 29(1):172-173; Kaplancikli et al. (2005) J Enzyme Inhib Med. Chem. 20(2):179-182; Jantova et al. (2004) Neoplasma 51(6): 436-441; and Fitzgerald et al. (2004) J Appl. Microbiol. 97(1):104-113). These methods can include measuring the turbidity (e.g., the optical density or OD) of a solution of bacteria following treatment with a compound compared to the turbidity of a solution of bacteria in control treatments. Turbidity can be measured using standard spectrophotomic devices (for example, the 8453 UV-Visible Spectrophotometer, Agilent Technologies, Palo Alto, Calif.) and reading an OD at, for example, 595 or 600 nanometers (nm). Additional methods include plating aliquots of the compound-treated or control-treated bacterial cultures on culture plates and counting the number of colonies that form. Alternative methods of determining (e.g., detecting or measuring) whether a compound (e.g., any of the compositions described herein) inhibits the growth of a microbial cell (e.g., a bacterial cell, a fungal cell, or a protozoan cell) can include, for example, Kirby-Bauer disk tests.

Methods of assessing the inhibitory activity of a composition of formula I, II, III, IV, V, VI, or VII against a microbial or cancer cell can be quantitative, semi-quantitative, or qualitative. Thus, for example, the level of a polypeptide's expression can be determined as a discrete value. An example of a quantitative determination of a compound's growth inhibitory activity is a Minimum Inhibitory Concentration (MIC) determination, which is a measure of the highest dilution (i.e., lowest concentration) of a growth inhibitory compound (e.g., and antibiotic, or anti-cancer agent) that completely inhibits the growth of an cell contacted thereby. Another quantitative measurement of the effectiveness of an inhibitor of cell growth is a 50% Inhibition Concentration, or IC50 value, which is the molar concentration of an agent (e.g., a compound, a composition having formula I, II, III, IV, V, VI, or VII) which gives one-half the maximal response of that agent. Alternatively, the growth inhibitory activity of a composition having formula I, II, III, IV, V, VI, or VII can be assessed using a variety of semi-quantitative/qualitative systems known in the art. Thus, the growth inhibitory activity of a composition of formula I, II, III, IV, V, VI, or VII against a microbial or cancer cell, can be expressed as, for example, (a) one or more of "excellent", "good", "satisfactory", "unsatisfactory", and/or "poor"; (b) one or more of "very high", "high", "average", "low", and/or "very low"; or (c) one or more of "+++++", "++++", "+++", "++", "+", "+/−", and/or "−". In this aspect, where it is also desired, growth inhibitory activity of a composition against a microbial or cancer cell can be expressed relative to the growth of the cell in the absence of the composition and/or the growth of the cell in the presence of the solvent or carrier in which the composition is delivered to the cell.

In another embodiment, the invention features a method of inhibiting the growth of a mammalian cancer cell (e.g., a human cancer cell). The mammalian cancer cell can be, for example, from a colon cancer, a breast cancer, a lung cancer, a prostate cancer, a bone cancer, or a liquid tissue cancer (i.e., a lymphoma or a leukemia). The cancer cell can be a clinical isolate obtained from a subject having the cancer, or can be a cell line (e.g., an immortalized cell line) generated in vitro using methods known to those of ordinary skill in the art.

Methods for determining the effect of test agents (e.g., compounds, a composition of matter having formula I, II, III, IV, V, VI, or VII) on the growth of cancer cells are well known to one of skill in the art. Cells are generally plated on solid support matrix (e.g., a plastic tissue culture plate, or a multiwell (96 or 386-well) tissue culture plate) and grown in appropriate medium. Cells are then contacted with serial dilutions of a test compound generally ranging, for example, from 10 µM to 0.1 µM concentration. Often, a control compound (e.g., a known inhibitor of known concentration) is also added to a set of cells as an internal standard. Often, a set of cells are grown in the presence of a carrier, buffer, or solvent, in which the compound is delivered. Cells are grown in the presence or absence of test compounds for varying times, for example, from 1 to three days (1 day, 2 days, 3 days, 4 days, 1 week, 2 weeks), followed by a test for the number of cells remaining on the plate or the viability of the cells remaining on the plate. Methods of detecting (e.g., determining or measuring) the extent of cancer cell growth inhibition by a compound are myriad and well known to those of ordinary skill in the art. These methods can include, for example, counting the number of cells remaining in the well after the period of treatment with the compound. In this method, cells can be trypsinized from the plate, washed, stained with a dye (e.g., typan blue), and counted using a microscope or mechanical cell counter (Beckman-Coulter Z1™ Series COULTER COUNTER® Cell and Particle Counter). Since dyes like trypan blue are only taken up by dead or dying cells, this method allows for discrimination (i.e., blue or white cell) between viable and non-viable cells in a population. Another method for determining cancer cell growth inhibition by a compound (e.g., any one of the compositions described herein) following treatment is a metabolic assay, for example, an MTT-metabolic assay (Invitrogen, USA). MTT Diphenyltetrazolium Bromide, is a tetrazolium salt (yellowish) that is cleaved to formazan crystals by the succinate dehydrogenase system which belongs to the mitochondrial respiratory chain, and is only active in viable cells. The mitochondrial succinate dehydrogenase reduces the MTT crystals into purple formazan in the presence of an electron coupling reagent. Following the treatment of the cells with a compound, the cells are exposed to the MTT reagent and the more viable cells are present in a well, the more formazan dye is produced. Extent of formazan dye can be measured, for example, using a spectrophotometer.

Other commonly used methods of testing for cancer growth inhibition by an agent (e.g., a compound or a composition described herein) include the monitoring of DNA synthesis. Cells grown in the presence or absence of compound are also treated with a nucleotide analog that can incorporate into the DNA of the cell upon cell division. Examples of such nucleotide analogs include, for example, BrdU or $^3$H-Thymidine. In each case, the amount of label incorporated into the cells (grown in the presence and absence of a given inhibitory agent) is quantitated, and the amount of label incorporation is directly proportional to the amount of cell growth in the population of cells.

Animal Models/In Vivo Methods

In some embodiments, the methods used to determine whether a compound (e.g., a composition described herein) inhibits the growth of a microbial cell can be in vitro methods (i.e., in cell culture, see above). In alternative embodiments, the methods used to determine whether a compound inhibits the growth of a microbial cell can be in vivo methods (i.e., performed in a whole organism, a whole animal, e.g., a mouse or a human). In such embodiments, compositions are delivered to an organism which is infected with a particular microbe (e.g., a microbial pathogen), and the effect of the composition on the growth of the microbe is determined in the context of the whole animal host. Examples of in vivo methods, for example, can be found in Furukawa et al. (2000) J. Antimicrob. Chemo. 46:443-450; Aoyagi et al. (1994) J. Antibiot. (Tokyo) 47(10):1077-1083; Brouillette et al. (2004) Vet. Microbiol. 101(4):253-262; Pinero et al. (2006) Acta Tropica 98(1):59-65; and Sharma et al. (2003) Antimicrob. Agents and Chemo. 47(12):3859-3866.

The following examples are intended to illustrate, not limit, the invention.

EXAMPLES

Example 1

Materials and Methods

All chemicals used in the study were obtained from Sigma-Aldrich (St. Louis, Mo., USA), Acros Organics, Fluka (Seelze, Germany), or TGI Organic Chemicals. All solvents used in the synthesis were anhydrous. Compound 24 was synthesized according to (25); compound 26—according to (Kauer et al. (1964) Am. Soc. 86:4732). Thin layer chromatography (TLC) was performed on Sigma-Aldrich TLC plates, column chromatography (20×2.5 sm)—on Kieselgel 60 (Fluka). UV spectra were recorded on UV160U spectrophotometer (Shimadzu). The collections of microbial pathogens were from the TB Center at the Public Health Research Instititute and from the laboratory of Dr David Perlin (PHRI, Newark, N.J.). The toxicity assays were performed on human macrophages using the MTT cell proliferation kit (Promega, Madison, Wis.) according to kit protocols.

ITC Synthesis, Protocol I (The Main Protocol). In an ice bath, and with stirring, 1 mmol of amino compound in 1-2 mL of chloroform was added drop-wise to a mixture of 1.3 mmol of thiophosgene and 3 mL of chloroform. For diamino compounds the amount of thiophosgene was doubled. After 5 minutes, the mixture was supplemented with anhydrous triethylamine (two equivalents per each amino group) in 1-2 mL of chloroform with continuous stirring. The mixture was brought to room temperature and supplemented with water (40 mL). After an extraction, the organic phase was collected and washed with another 40 mL of water, and then evaporated in vacuo. The residue was dissolved in 3-4 mL of acetone and the solution mixed with 6-8 ml of silicagel in a round bottom flask. The silicagel was dried in vacuo and applied on top of silicagel column (20×2.5 sm) equilibrated with a mixture of hexane/acetone (3:1 to 1:1 for different compounds). The product was eluted by the same composition of solvents at an elution rate of ~100 ml/h. Fractions containing the product were detected by UV light, combined, and subsequently evaporated under reduced pressure. Most of the residues represented viscose oils, only a few of them being crystals. The products were collected and stored at −20°.

ITC Synthesis, Protocol II (for Compounds 29-32, 34 and 36). One mmol of amino compound was dissolved in 0.5 mL of methylene chloride. This solution was added drop-wise to a solution of 1.1 mmol of thiocarbonyldiimidazole in 2 mL of the same solvent, followed by addition of 2.2 equivalents of triethylamine. After 20 minutes, the mixture was washed twice with 3 mL of water, the organic phase was collected and evaporated, and lastly, the product was purified by chromatography on silicagel column as in the previous protocol.

ITC Synthesis, General Protocol for Homolos of Hydroxy-ITC Compounds. A synthetic method was developed for making homologs of hydroxyl-ITC compounds from their corresponding dibromoalkanes, using the steps described below.

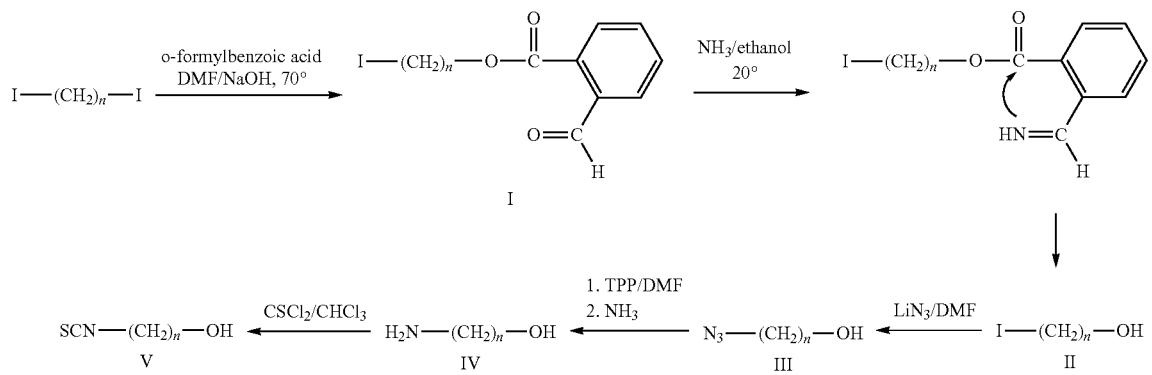

Compound I: Into 7 mL of dimethylfuran (DMF) was dissolved 3.6 mmol of o-formylbenzoic acid, and supplemented with one equivalent of NaOH powder. The mixture was stirred at 70° C. until completely dissolved, followed by addition of 5.2 mmol (1.1 mL) of diiodooctane. The stirring was continued at 70° C. for 30 minutes, followed by additional of 40 mL of water and centrifugation. The solvent was discarded and the residue dissolved in chloroform and fractionated on a silicagel column in hexane:acetone (4:1) as described above. Main product fractions were combined and evaporated in vacuo.

Compound II: Product I was dissolved in 3 mL of alcohol and supplemented with 0.5 mL of ammonium hydroxide and 20 μl of TFA. After 30 to 60 minutes, the volatile products were removed by evaporation in vacuo. The residue was supplemented with 20 mL of water and 0.5 mL of 10 M NaOH, and the product was then extracted using 30 mL of ether. The solvent was removed by evaporation and the residue additionally evaporated with acetonitrile a few times to remove the traces of water.

Compound III: Product II was added to a solution of 120 mg of lithium azide dissolved in 0.7 mL of DMF, and maintained at 70° for 20 minutes. Following the 20 minute incubation, the mixture was supplemented with 6 mL of water, and the product extracted with ether. The solvent was removed in vacuo, followed by additional evaporations with acetonitrile, when necessary.

Compound IV: Compound III (310 mg) was mixed into a solution of 520 mg of triphenylphosphine (TPP) in 3 mL of DMF. The mixture was held for 10 min at 20° C. and then for 10 to 15 min at 50° C. Following the incubations, 1.5 mL of ammonium hydroxide was added to the mixture and the incubation continued at 50° for another 30 minutes. The mixture was diluted with 20 mL of 1 M citric acid and extracted with ether. Seven mL of 10 M NaOH were added to the water phase, and the product extracted with ethylacetate (3×15 ml). The organic phase was evaporated in vacuo and after the major portion of the solvent was removed the evaporation continued at 70° to remove the traces of DMF.

Compound V: was synthesized from the product IV using protocol I (see above).

ITC Synthesis. Protocol for the Synthesis of Fluorescent ITC Compounds 59, 67, 68 and 69. The synthetic method for making Fluorescent ITC compounds is presented below.

mL of water. After partitioning, the organic phase was evaporated to dryness, the residue was dissolved in acetone and processed as described above before application on silicagel column (see Protocol I). Then the product was purified by chromatography using hexane/acetone (4:1) eluent.

Compound II: Fifty mg (130 μmol) of was mixed with the solution of 8 mg (160 μmol) of lithium azide in 100 μL of DMF. After incubation for 5 minutes at 50° C., the mixture was cooled to room temperature and supplemented with 40 mg of TPP. Following an additional incubation for 20 minutes at 60° C., 20 μL of ammonium hydroxide was added and the incubation continued at the same temperature. After 20 minutes, 400 μL of 1 M citric acid was added and the mixture extracted with ether. One hundred μl of 10 M KOH was subsequently added, and the product was extracted with ethyl acetate (4×700 μl). The solvent was evaporated in vacuo.

Compound III: The product of the above compound II step, was dissolved in 0.6 mL of chloroform and supplemented with 1.5 equivalents of thiocarbonyldiimidazole, followed by addition of 10 μL of TFA. After a 1 hour incubation at 50° C., the solvent was removed by evaporation and the product purified by chromatography on silicagel column using Hexane/acetone (3:1) as eluent.

Figure 6:
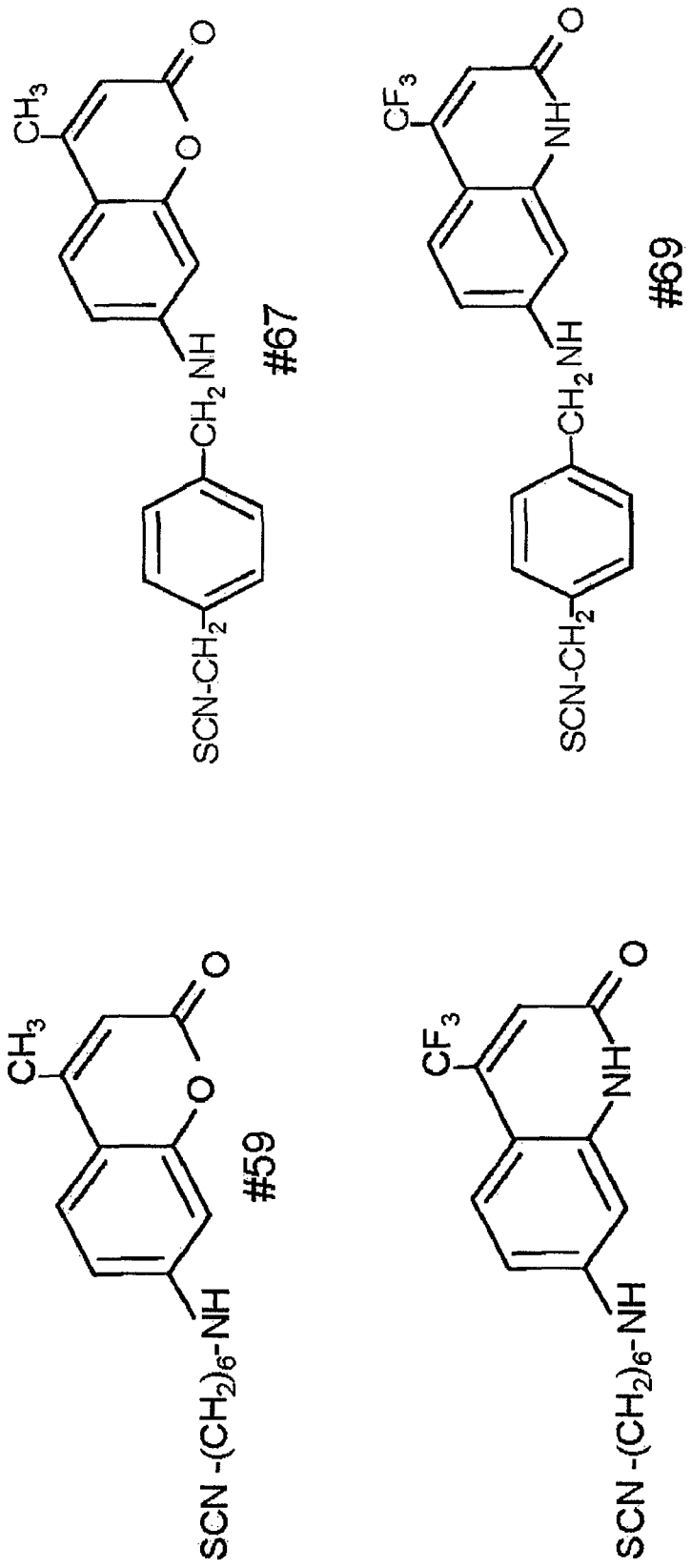
FIG. 6 is a depiction of the chemical structures of several novel, fluorescent ITC compounds: Compounds 59, 67, 68, and 69.

Compound 67 of FIG. 6 (as well as other fluorescent ITC compounds of FIG. 6) were synthesized using the same strategy.

Preincubation of Compound 37 in Culture Medium and Its Effect on Growth-Inhibitory Activity. Compound 37 was added to liquid Muller-Hinton Broth (MHB) medium in microtiter plate to final concentration 2 mg/ml and incubated for the periods of time indicated in FIG. 5 before addition to

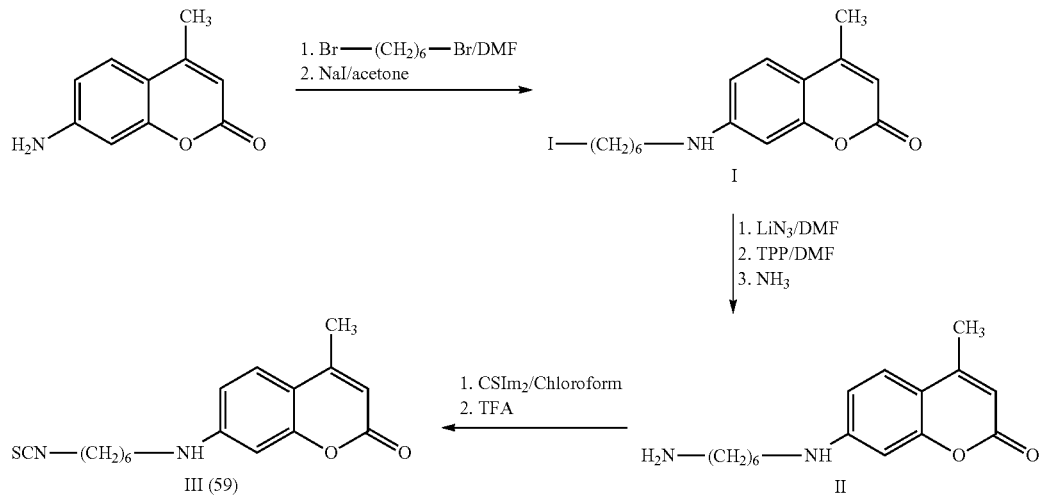

Compound I: To generate compound I, 130 mg (0.75 mmol) of 7-amino-4-methylcoumarine were dissolved in 0.7 ml of DMF and supplemented with 0.4 ml (2.4 mmol) of 1,6-dibromohaxane and 100 mg of sodium bicarbonate. After incubation at 60° C. for 18 to 20 hours, excess 1,6-dibromohaxane was removed by extraction with hexane (3×5 ml), and the residue was isolated by centrifugation. A resulting solution was prepared with the product and 2 to 3 mL of 20% NaI in acetone. After incubation for 10 min at 50° C., the acetone was removed by evaporation in vacuo and the residue was supplemented with 5 mL of ether and 5 cultures of B. cereus. After incubation for 20 h at 37° C., bacterial growth was assessed by measuring of the turbidity at 600 nm.

Determination of the Bactericidal and Bacteriostatic Activities of Compound 37. Compound was added to the cultures of *B. cereus* containing $2\times10^4$ CFU at the concentrations indicated in FIGS. 2A and 2B. Following incubation for 2 h at 37° C., the number of surviving cells was determined by a serial dilution method and subsequent plating onto the MHA media without ITC compound. CFU were counted after 1 and 3 days incubation at 37° C.

Example 2

Synthesis of Novel ITC Compounds

The structure of the compounds tested in this study are presented in Table 1, and include ITCs synthesized in this work. The majority of the ITC compounds were synthesized by treatment of the corresponding amines with thiophosgene (Dyson (1937) Org. Synth. Coll. 1:158) in the presence of proton acceptor. In some cases, thiocarbonyldiimidazole was used instead of thiophosgene to avoid side reactions. The purity and identity of the newly synthesized compounds were confirmed by chromatography, UV and NMR-spectroscopy, and by quantitative test-reaction with ammonium hydroxide which leads to corresponding thiourea derivatives. FIG. 1 depicts a typical UV spectrum of an aliphatic ITC compound, which displays the absorption maximum at 238 nm ($\epsilon_{238}$ 910 $M^{-1}$ $sm^{-1}$) as expected (Zhang et al. (1992) Proc. Natl. Acad. Sci. USA 89:2399-2403). As further shown in FIG. 1, treatment with ammonium hydroxide results in the dramatic increase of the absorption at 238 nm characteristic for thiourea derivatives ($\epsilon_{238}$ 16 800 $M^{-1}$ $sm^{-1}$). The reaction products resulting from ammonium hydroxide treatment migrate much slower on TLC than the ITC compounds not reacted with ammonium hydroxide. For bifunctional ITC compounds (i.e., those ITC compounds with two ITC substituents), an intermediate reaction product containing one thiourea group per molecule was detected upon incubation with ammonium hydroxide. Aromatic compounds, whereby the ITC group is directly attached to the aryl moiety (e.g., Compound 4 of Table 1), were about 10 times more reactive that those containing aliphatic groups adjacent to the ITC moeity.

TABLE 1

Structure and general antimicrobial activity of studied ITC and related compounds.

| # | Structure | General antimicrobial activity | Synthetic protocol |
|---|---|---|---|
| | Aliphatic ITC derivatives | | |
| 8. | $CH_3$—N=C=S | +/− | ** |
| 22. | $CH_2$=$CH_2CH_2$—N=C=S | +/− | ** |
| 7. | $CH_3CH_2CH_2CH_2$—N=C=S | +/− | ** |
| | Hydroxy- ITC derivatives | | |
| 18. | HO—$(CH_2)_4$—N=C=S | + | ** |
| 5. | HO—$(CH_2)_5$—N=C=S | ++ | I |
| 21. | HO—$(CH_2)_6$—N=C=S | +++ | I |
| 44. | HO—$(CH_2)_7$—N=C=S | ++++ | I |
| 45. | HO—$(CH_2)_8$—N=C=S | ++++ | I |
| | Bifunctional ITC derivatives | | |
| 38. | S=C=N—$(CH_2)_4$—N=C=S | + | I |
| 39. | S=C=N—$(CH_2)_5$—N=C=S | ++ | I |
| 40. | S=C=N—$(CH_2)_6$—N=C=S | ++++ | I |
| 41. | S=C=N—$(CH_2)_7$—N=C=S | +++++ | I |
| 42. | S=C=N—$(CH_2)_8$—N=C=S | +++++ | I |
| 43. | S=C=N—$(CH_2)_2$—O—$(CH_2)_2$—O—$(CH_2)_2$—N=C=S | + | I |
| 37. | S=C=N—$CH_2$—C$_6$H$_4$—$CH_2$—N=C=S | +++++ | I |
| 16. | S=C=N—$CH_2$—C$_6$H$_4$—N=C=S | +++ | I |
| | Aromatic and heterocyclic ITC derivatives | | |
| 4. | C$_6$H$_5$—N=C=S | +/− | ** |
| 1. | C$_6$H$_5$—$CH_2$—N=C=S | ++ | ** |
| 17. | C$_6$H$_5$—$COH_2CH_2$—N=C=S | ++ | ** |
| 3. | $CH_3O$—C$_6$H$_4$—N=C=S | + | ** |
| 2. | $CH_3O$—C$_6$H$_4$—$CH_2$—N=C=S | +++ | ** |

TABLE 1-continued
Structure and general antimicrobial activity of studied ITC and related compounds.
| # | Structure | General antimicrobial activity | Synthetic protocol |
|---|---|---|---|
| 20. | 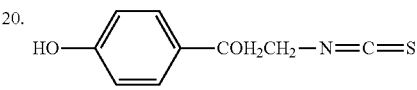 | ++++ | ** |
| 27. | 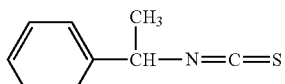 | +/− | I |
| 19. | 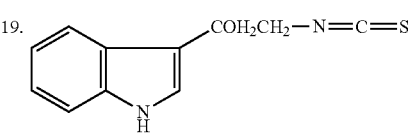 | +++ | I |
| 34. | 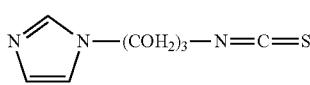 | ++ | II |
| 29. | 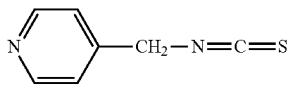 | − | II |
| 30. | 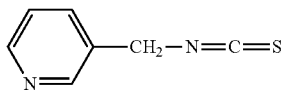 | ++++ | II |
| 31. | 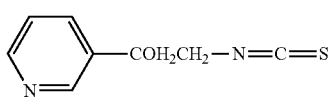 | + | II |
| 32. | 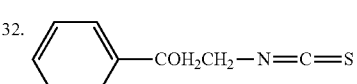 | +++ | II |
| 35. | 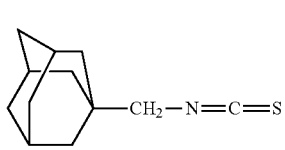 [SMILES: S=C=NCC12CC3CC(CC(C3)C1)C2] | +/− | I |
| 14. | 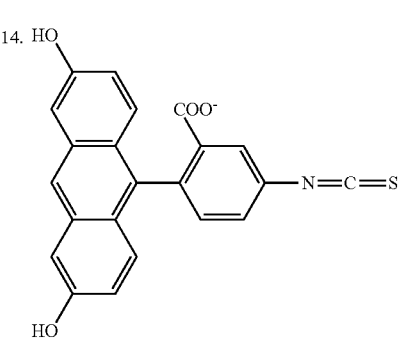 | + | ** |
| 33. | 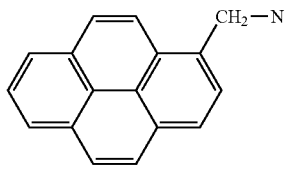 | + | I |

TABLE 1-continued

Structure and general antimicrobial activity of studied ITC and related compounds.

| # | Structure | General antimicrobial activity | Synthetic protocol |
|---|---|---|---|
| | Control compounds | | |
| 23. | 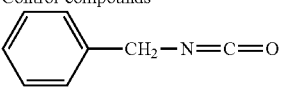 | – | ** |
| 25. | 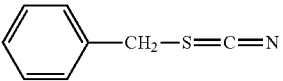 | – | ** |

*Deduced from the number of sensitive bacterial species and average MIC
**Known compounds

Example 3

Potent Anti-Microbial Activity of Selected ITC Compounds

The growth inhibitory effect of a number of various ITC compounds were tested on large collection of clinical isolates of bacteria and fungus (including yeasts), in order to establish a systematic structure-activity relationship for the ITC compounds. Compounds 2 and 20—two of the most active monofunctional ITC compounds (Swart et al. (2002) Bioorg. Med. Chem. Lett. 12:2435-2437; Tajima et al. (1998) Biosci. Biotechnol. Biochem. 62:491-495)—were used as reference compounds for the tests. To assess the average activity for an individual ITC compound, the semi-quantitative score was calculated for each compound based on the number of sensitive bacterial strains at concentrations of 100 and 200 µM. The results of this preliminary evaluation of the compounds are presented in the Table 1 and range from "–," indicating no activity, to "+++++," indicating highest activity. As shown in FIG. 1, ITC compounds containing small hydrocarbon chains (e.g., ITC derivatives 8, 22, 7) displayed very little activity. However, the addition of a terminal hydroxyl group to Compound 7 (yielding Compound 18) increased its potency. For this class of hydroxyl-ITC compounds, increasing the length of the spacer between the hydroxyl and ITC functional groups from 4, up to 8 carbons (e.g., compounds 18, 5, 21, 44 and 45) greatly enhanced their efficacy.

Next, compounds containing two ITC functional groups (or bifunctional ITC compounds) were tested. For bifunctional ITC compounds, the activity increased progressively with the size of connecting carbon spacer (see compounds 38-42). The most active compound from this series was Compound 42 containing an 8 carbon spacer between the two ITC functional groups. Substitution of two carbons in the spacer with oxygen (Compound 43), while preserving the size and geometry of the spacer, greatly reduced the activity. In contrast, replacing four methylene groups in compound 40 with a bulkier phenylene group (Compound 37), further increased the inhibitory activity. Deletion of one of methylene group in the spacer (Compound 16) negatively affected the activity.

Some aromatic ITC compounds have known growth inhibition properties. Compound 1, a benzyl-ITC compound, was used as a reference compound for this class. In control experiments, a crucial role for the ITC functional group itself in inhibition of microbial cell growth was established. Neither of the chemically related derivatives—isocyanate (Compound 23) or thiocyanate (Compound 25)—displayed any activity at concentrations matching the Compound 1.

Deletion of a methylene group from Compound 1 (resulting in Compound 4) strongly decreased the activity, while insertion of extra methylene group in Compound 1 (resulting in Compound 17) had no detectable effect. The presence of a hydroxy- or methoxy group at the para-position of the phenyl ring (see, for example, Compounds 2, 3 and 20) increased the antibacterial activity of the ITC compounds. Furthermore, introduction of substituents to the Cl methylene group adjacent to the ITC group of Compound 1 (resulting in Compound 27) strongly decreased the inhibitory potential compared to Compound 1.

Heterocyclic ITC compounds exhibited different levels of inhibitory activity. Indole- (e.g., Compound 19) and pyridine-derivatives (e.g., Compounds 30 and 32) were generally more active than imidazole-containing ITC derivatives (Compound 34). The activity of pyridine derivatives was strictly dependent on the position of nitrogen in the ring, and the size of methylene spacer between the ITC functional group and the ring. Placing the nitrogen at the para-position (Compound 29) decreased the activity relative to the reference Compound 1, while a meta-substitution (Compound 30) resulted in much better inhibition of microbial growth. One explanation for the effect of a nitrogen at the para-position of the pyrimidine ring could be explained by instability of the compound seen in independent experiments. Insertion of an extra methylene group in the spacer connecting the phenyl ring with the ITC functional group in this series of compounds (compare Compounds 30 and 31) dramatically decreased their efficacy, while having nothing to do with the activity of the non-substituted parent compound (compare compounds 1 and 17). Compound 32, which contains nitrogen at the ortho-position was much more active than the corresponding meta-derivative (Compound 31). Remarkably, the distance between the ring nitrogen and the ITC functional group in Compound 31 is the same as the highly potent ITC Compound 30. Finally, ITC compounds containing large polycyclic carriers (e.g., Compounds 14, 33 and 35) displayed poor growth-inhibitory activity.

Example 4

Growth Inhibitory Activity of Selected ITC Compounds Against Specific Classes of Pathogens As indicated above, the General Antimicrobial Activity score presented in Table 1 represents the average inhibitory effect of a compound on a broad range of bacterial species, but the activity of individual ITC compounds against particular bacterial species can vary significantly from the average. This is illustrated by FIG. 2, which shows the activity of the ITC compounds against *Bacillus cereus*. Compound 33, for example, while exhibiting a low average activity represented in Table 1, is very efficient against *Bacillus cereus* (FIG. 2), *Staphylococcus epidermidis*, methicillin-resistant *Staphylococcus aureus* (MRSA) (data not shown), as well *Cryptococcus neoformans* (see below). The same was true for Compound 38. In contrast, Compound 30, which possessed a high overall activity as shown in Table 1, was only moderately active against *Bacillus cereus*.

Next, the Minimal Inhibitory Concentration (MIC)—the minimum concentration of the compound that completely inhibits the growth of a microorganism at 24 hours of incubation, expressed in units of μg/mL—was determined for the most active newly-synthesized (bifunctional) ITC compounds and reference compounds 2 and 20. These MIC data were generated for 24 different strains of bacteria, including gram positive and negative bacteria, grown in or on Muller-Hinton Broth (MHB) and Tryptic Soybean agar, and summarized in Table 2 below.

TABLE 2

Inhibitory Activity (MIC values) of Several ITC Compounds on Gram Positive and Gram Negative Bacteria.

| Strain | Gram-type | Compound | | | | | |
|---|---|---|---|---|---|---|---|
| | | #2 | #20 | #37 | #41 | #42 | #44 |
| *Acinetobacter* sp., BK12786 | − | >64 | >64 | >64 | 32 | >64 | 64 |
| *Acinetobacter* sp., BK12787 | − | >64 | >64 | >64 | 32 | >64 | 64 |
| *Enterobacter cloacii* BK12313 | − | >64 | >64 | >64 | >64 | 64 | >64 |
| *Enterobacter cloacii* BK12315 | − | >64 | >64 | >64 | >64 | 64 | >64 |
| *Escherichia coli* BK12336 | − | >64 | >64 | 8-16 | >64 | >64 | >64 |
| *Escherichia coli* K12 | − | 64 | >64 | 16 | >64 | >64 | >64 |
| *Klebsiella pneumonii* BK12260 | − | >64 | >64 | >64 | >64 | >64 | >64 |
| *Klebsiella pneumonii* BK12261 | − | >64 | >64 | >64 | >64 | >64 | >64 |
| *Pseudomonas aeruginosa* BK12347 | − | >64 | >64 | >64 | 64 | >64 | >64 |
| *Pseudomonas aeruginosa* BK12348 | − | >64 | >64 | >64 | 64 | >64 | >64 |
| *Serattia marcescens* BK12421 | − | >64 | >64 | 64 | >64 | 64 | >64 |
| *Serattia marcescens* BK12426 | − | >64 | >64 | 64 | >64 | 64 | >64 |
| *Shigella* sp., BK 12440 | − | 64 | 32-64 | 16 | 64 | >64 | 64 |
| *Shigella* sp., BK 12441 | − | 32-64 | 32-64 | 16 | 64 | >64 | 64 |
| *Bacillus cereus* 4342 | + | 32 | 16 | 2 | 2 | 2 | 8 |
| *Bacillus subtilis* BK11590 | + | 32-64 | 16-32 | 4 | 2 | 2 | 4 |
| *Enterococcus* sp., BK11936 | + | 64 | 32 | 16 | 8 | 8 | 32 |
| *Enterococcus* sp., BK11940 | + | 64 | 32 | 16 | 8 | 8 | 32 |
| MRSA (*Staphylococcus aureus*) BK12060 | + | 32-64 | 32 | 8 | 4 | 2-4 | 8 |
| MRSA (*Staphylococcus aureus*) BK12064 | + | 64 | 32 | 4 | 4 | 4 | 16 |
| *Staphylococcus epidermidis* BK12798 | + | 32 | 16-32 | 0.5 | 4 | 2 | 8 |
| *Staphylococcus epidermidis* BK12799 | + | 32 | 16-32 | 0.5 | 1 | 2 | 8 |
| *Streptococcus* sp., BK12233* | + | 4 | 2 | <0.5 | 1-2 | 1-2 | ND |
| *Streptococcus* sp., BK12235* | + | 8 | 4 | <0.5 | 1-2 | 2 | ND |

*indicates that the bacteria were grown on Tryptic Soy agar medium

BK# refers to the identification number of indicated bacterial strains in PHRI TB Center Bacterial Strains Collection.

MIC or Minimum Inhibitory Concentration values (i.e., the minimum concentration of a compound required to completely inhibit the growth of a given microorganism) are given in terms of μg/mL Table 2 indicates, for example, that (1) certain tested ITC compounds, generally, are more active against Gram-positive (G$^+$) than against Gram-negative (G$^-$) bacteria, with the most sensitive strains being Staphylococci, Streptococc,i and Bacilli. However, Compound 37, for example, is also effective against some G$^-$ strains. Although Compounds 42 and 44 are highly discriminative for G$^+$ bacterial strains, this suggests that the bifunctional ITC compounds may have a broad range of activity; (2) certain bifunctional ITC compounds are more efficient against some bacteria in Tryptic Soybean rather than in Muller-Hinton media (compound 30) while the others exhibit the same level of activity in both media; and (3) several of the bifunctional compounds synthesized in the present study are 2-32 times more active than the control compounds (Compounds 2 and 20) tested in the present study.

Next, several of the bifunctional ITC compounds were tested for their ability to inhibit the growth of some clinical isolates of *Mycobacteria*, the results of which are summarized in Table 3 below. Table headings are the same as indicated in Table 2.

TABLE 3

Activity (MIC, μg/ml) of selected inhibitors against *Mycobacteria*

| Strain | Compound | | | | | | | | |
|---|---|---|---|---|---|---|---|---|---|
| | #2 | #20 | #30 | #37 | #40 | #41 | #42 | #45 | Rif |
| *M. intracellularie* | 32 | 32 | 32 | 32 | 32 | 32 | 32 | 4 | 0.5 |
| *M. avium* | 32 | 32 | 32 | 32 | 32 | 32 | 32 | 4 | 0.5 |
| *M. scrofulaceum* | 32 | 32 | 32 | 16 | 32 | 32 | 32 | 8 | 0.5 |
| *M. cansassi* | 32 | 32 | 32 | 4 | 8 | 8 | 4 | 1 | 0.5 |
| *M. fortuitum* | 32 | 16 | 16 | 32 | 16 | 32 | 32 | 4 | >4 |
| *M. tuberculosis* W4 | ND | ND | ND | 2 | 2 | 2 | 4 | 1 | 0.5 |
| *M. tuberculosis* 210 | ND | ND | ND | 2 | 2 | 4 | 4 | 1 | 0.5 |
| *M. tuberculosis* W | 8 | 4 | 4 | 1 | 0.5 | 2 | 4 | 1 | >4 |
| *M. tuberculosis* H37Rv | 32 | 16 | 32 | 2 | 2 | 2 | 4 | 1 | 0.5 |
| *M. tuberculosis* CDC1551 | 32 | 16 | 16 | 4 | 4 | 2 | 8 | 2 | 0.5 |
| *M. tuberculosis* P | 8 | 4 | 4 | 2 | 2 | 4 | 4 | 2 | >4 |
| *M. tuberculosis* AB | ND | ND | ND | 2 | 4 | 2 | 4 | 2 | 0.5 |
| *M. bovis* BCG | ND | ND | ND | 2 | 2 | 2 | 4 | 0.5 | 0.5 |

ND not determined

These data indicate that the tested ITC compounds are very active against several strains of *M. bovis* and *M. tuberculosis*. Compound 45 demonstrated the highest activity, which inhibited the growth of all species of *Mycobacteria* including multi drug resistant (MDR) strains. Again, the average activity of newly-synthesized (bifunctional) ITC compounds of the study was 2-32 times better than that for the control compounds 2 and 20. Remarkably, the activity of some compounds was reproducibly grater towards MDR, than sensitive strains.

To determine whether the newly-synthesized (bifunctional) ITC compounds could inhibit the growth of other, non-bacterial microorganisms, the activity of several ITC compounds was determined against several fungal organisms, including yeasts. The results of these studies are presented in Table 4. It is seen that compounds synthesized in this study efficiently inhibit the growth of the pathogens, being generally more active comparing not only to the known ITCs but also to typical fungicide—Fluconazol. Again the ITCs were equally active against both MDR and sensitive strains.

TABLE 4

Anti-Fungal Activity (MIC) of Several ITC Compounds

| Fungal Organism | Compound | | | | | | | |
|---|---|---|---|---|---|---|---|---|
| | #2 | #20 | #30 | #33 | #37 | #41 | #45 | Fluc |
| *Candida albicans* 5108$^{mdr}$ | 2 | 4 | 0.5 | >64 | 0.5 | 8 | 4 | 32 |
| *Candida crusei* 6258$^{mdr}$ | 2 | ND | 0.5 | >64 | 0.5 | 2 | 4 | 32 |
| *Candida parapsilosis* 22019 | 4 | ND | 1 | 32 | 0.5 | 2 | 8 | 2 |
| *Candida albicans* 90028 | 4 | ND | 2 | 32 | 0.5 | 8 | 8 | 0.25? |
| *Candida albicans* 90030 | 4 | ND | 1 | 8 | 0.5 | <1 | 4 | 4 |
| *Candida dlabrata* 250$^{mdr}$ | 1** | ND | 2** | 64 | 0.125** | <1 | 4** | >64 |
| *Cryptococcus neoformans* CNH99 | <1 | ND | 1 | 4 | <1 | <1 | <1 | 4 |
| *Aspergillus fumigatus* Rit 1 | 8 | 4 | 4 | >64 | 0.5 | 4 | 8 | >64 |
| *Aspergillus fumigatus* Rit 11 | 8 | 4 | 4 | >64 | 0.5 | 4 | 8 | >64 |
| *Aspergillus fumigatus* Rit 21 | 8 | 4 | 4 | >64 | 0.5 | 4 | 8 | >64 |

**indicates that the MIC values were determined at 48 hours of growth.
ND indicates that the MIC value for the indicated compound was not determined for the indicated organism.
All other Table headings are the same as indicated for Tables 2 and 3.

Example 5

Bifunctional ITC Compounds have Both Bactericidal and Bacteriostatic Effects

Certain monofunctional ITC compounds have been shown to exhibit bactericidal action on *Helicobacter pylori*, while having a mostly bacteriostatic effect on *Escherichia* coli (Tajima et al. (1998) Biosci. Biotechnol. Biochem. 62:491-495; Tajima et al. (2001) Biosci. Biotechnol. Biochem. 67:1844-1846).

Figure 2A:
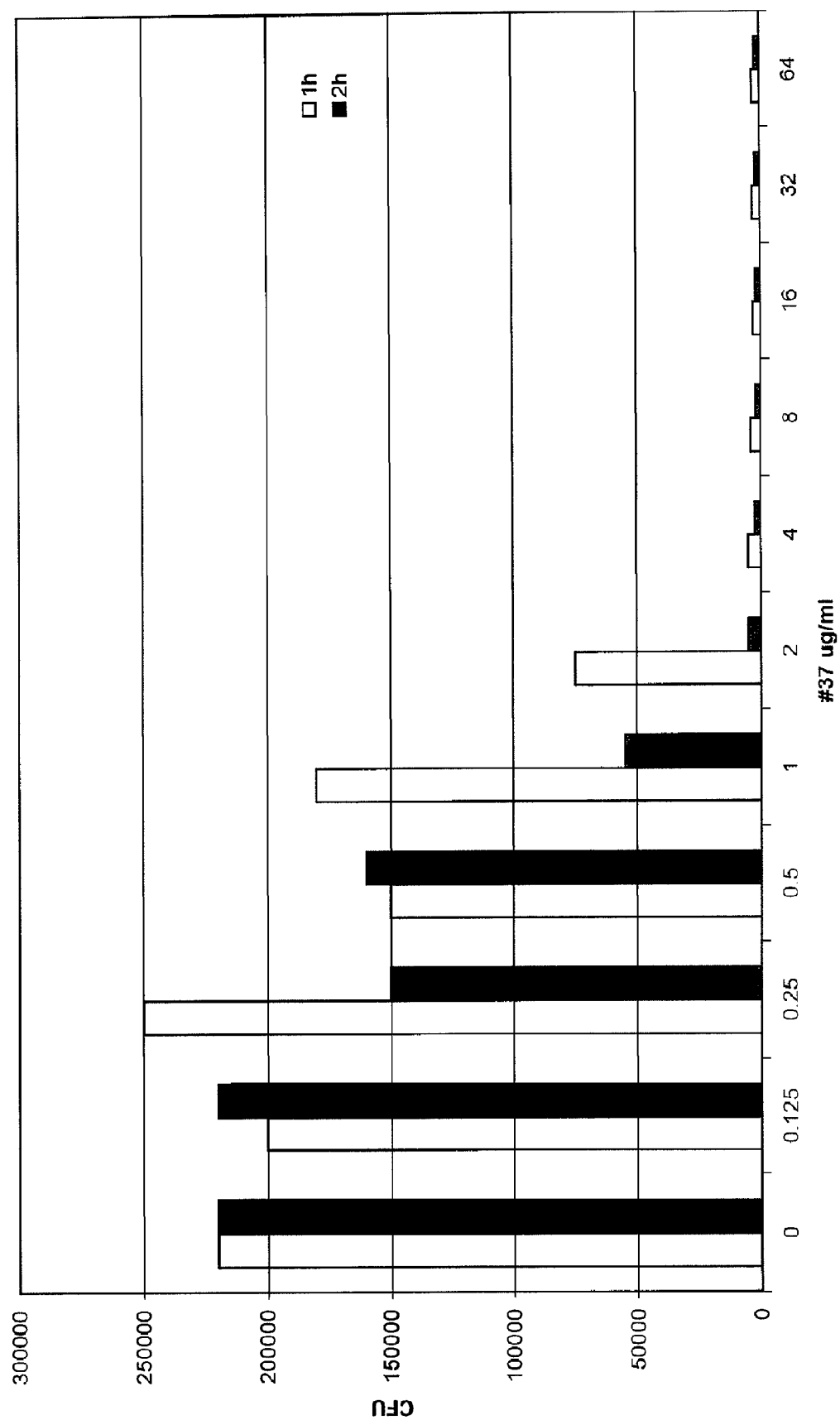
FIG. 2A is a bar graph depicting the bactericidal potency of Compound 37 on *Bacillus cereus* at different concentrations of compound at 1 and 2 hours exposure. The X-axis represents the concentration of Compound 37 used (in µg/mL), and the Y-axis is the Colony-Forming Units or CFU at each given concentration and at the indicated time.
Figure 2B:
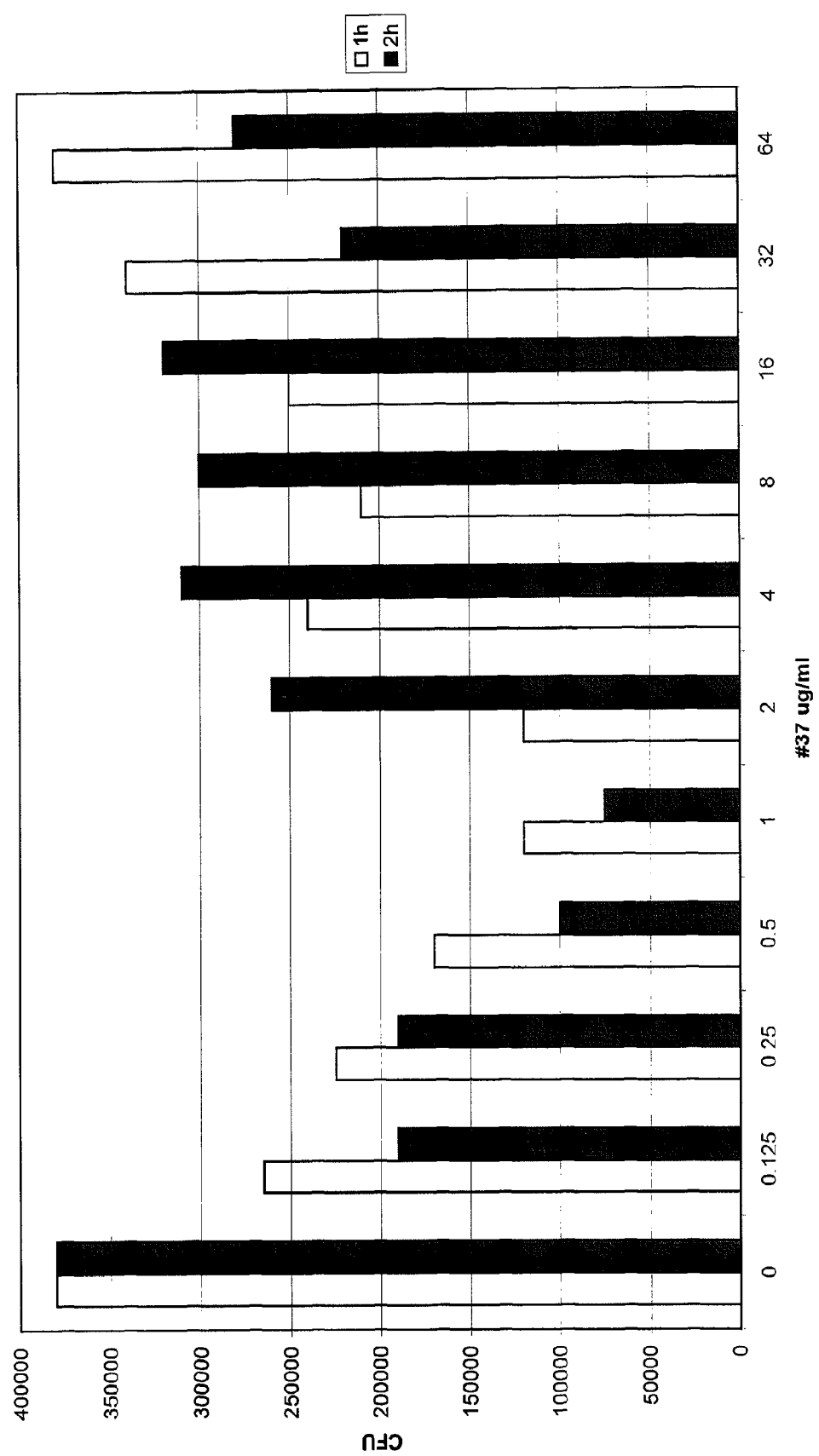
FIG. 2B is a bar graph depicting the bacteriostatic potency of Compound 37 on *Staphylococcus aureus* at different concentrations of compound at 1 and 2 hours exposure. The X-axis represents the concentration of Compound 37 used reported in ug/mL, and the Y-axis is the Colony-Forming Units or CFU at each given concentration and at the indicated time.

To determine whether the bifunctional compounds of the study exhibited bactericidial or bacteriostatic activity, the affect of one of the most potent bifunctional ITC compounds (Compound 37) was tested on representative bacterial Gram+ pathogens: *Bacillus cereus* and *Staphylococcus aureus*. Bacterial cells were cultured with and without varying concentrations of Compound 37 for 1 to 2 hours, and the amount and viability of surviving cells were determined following the incubation with compound 37. As shown in FIG. 2A, incubation of *Bacillus cereus* with Compound 37 resulted in a dramatic decrease in cell viability and no bacterial growth was detected at 20 h in the presence of Compound 37 at 4 µg/ml (data not shown). In contrast, Compound 37 exhibited a bacteriostatic effect on *Staphylococcus aureus* cultures as shown in FIG. 2B.

Example 6

Inhibition of Growth of THP1 Cells By Selected ITC Compounds

Figure 3:
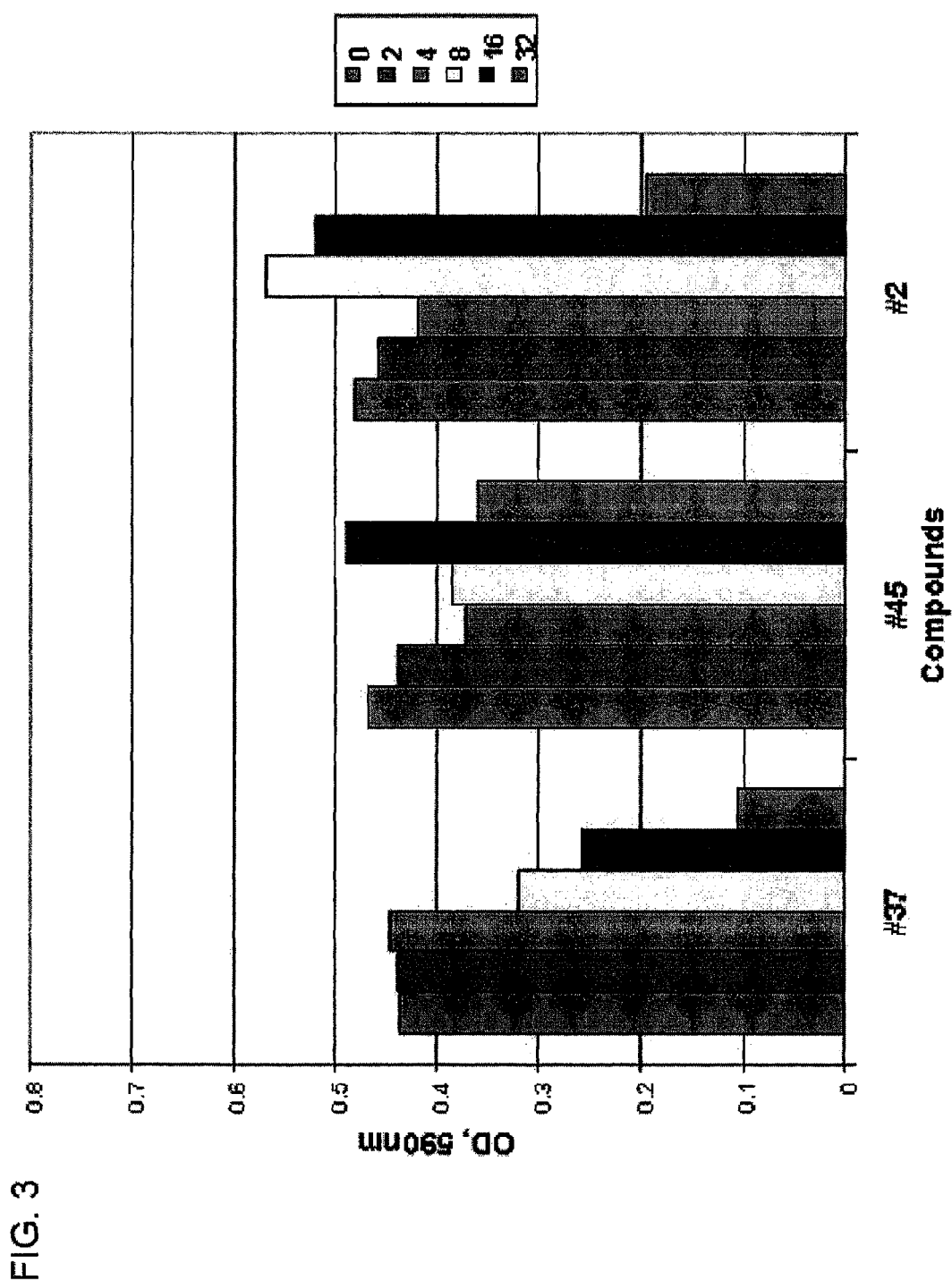
FIG. 3 is a bar graph depicting the growth-inhibitory activity of compounds 37, 45, and 2 on the THP1 cancer cell line in culture. THP1 cells were treated with 0, 2, 4, 8, 16, and 32 ug/mL of each of the compounds as indicated. The Y-axis represents the Optical Density (OD) for the wavelength 590 nm, as an indication of the fluorescence MTT growth assay.

Some epidemiological studies have established reliable correlation between the dietary intake of ITC compounds and decreased risk of cancer, and some biochemical studies have demonstrated that ITC compounds have selective apoptotic activity against certain cancer cells (Michaud et al. (1999) J. Natl. Cancer Inst. 91:605-613; Zhang et al. (1994) Cancer Res. 54:1976s-1981s; Hecht et al. (2000) Drug Metab. Rev. 32:395-411; Conaway et al. (2002) Curr. Drug Metab. 3:233-255; Talalay et al. (2001) J. Nutr. 131:3027S-3033S; and Zhang et al. (2003) Mol. Cancer Ther. 2:1045-1052). To determine if the novel ITC compounds possessed anti-cancer activity, the growth of human acute monocytic leukemia cells (THP1 cells), was examined in the presence of new compounds 37 and 45. THP1 cells were either mock-treated (DMSO vehicle alone), or treated with increasing doses of new compounds 37 and 45, from 0 to 32 µg/mL. Cells were incubated in the presence of compound for 24 hours, and subsequently were assayed for total cell viability using an MTT, metabolic assay. As shown in FIG. 3, treatment of THP1 cells with 8 µg/mL of compound 37 caused significant drop (~25%) in cell viability compared to the control compound 2. Higher dosages were even more potent on cell viability. In contrast, compound 45 was not able to affect the growth of THP1 cells even at the highest dosage of 32 µg/mL.

Example 7

Cytotoxicity of Selected ITC Compounds Towards Cultured Human Monocytes

Figure 4:
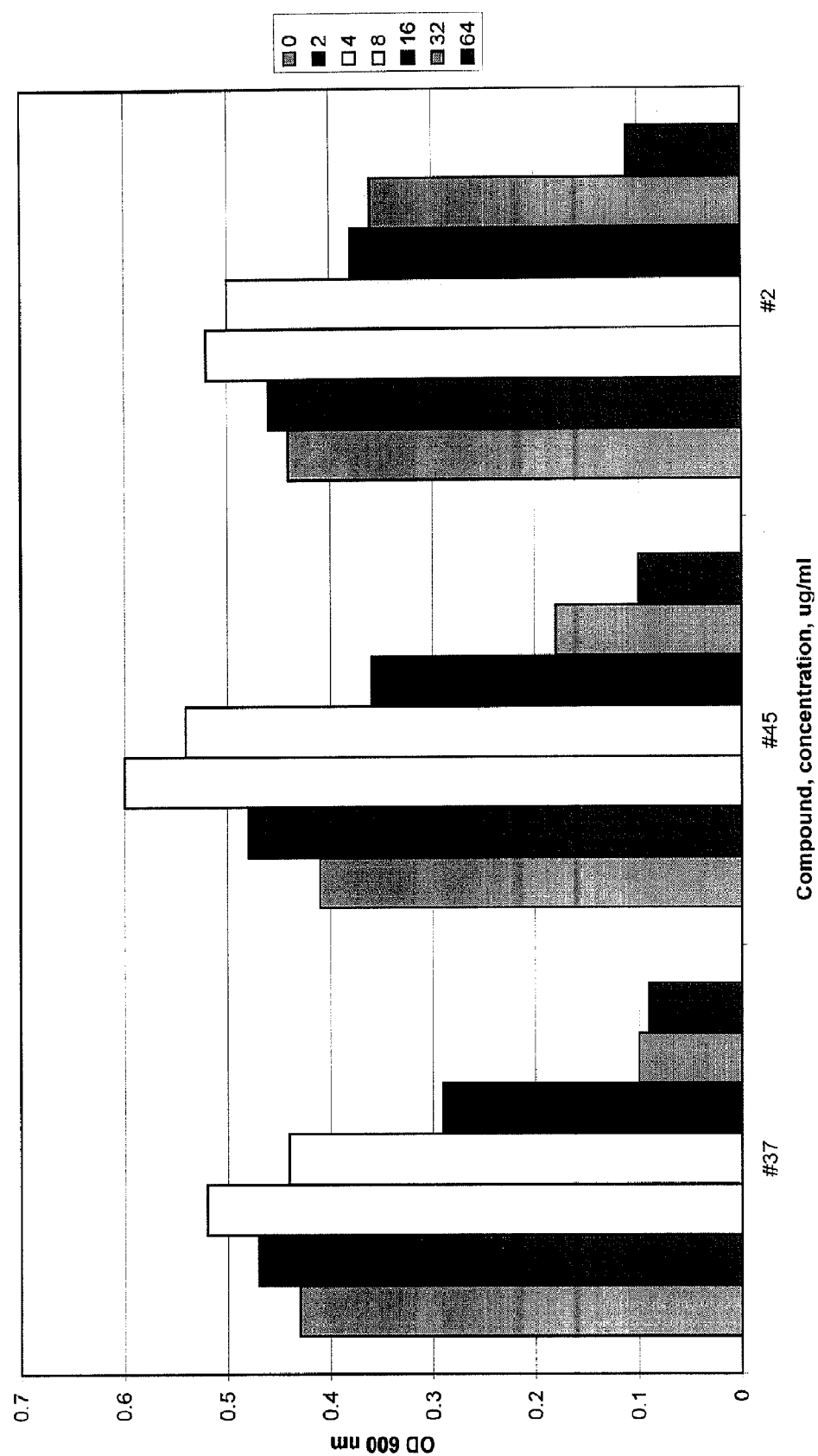
FIG. 4 is a bar graph depicting the toxicity of compounds 37, 45, and 2 on normal human macrophage cell primary isolates. The cells were treated with 0, 2, 4, 8, 16, and 32 ug/mL of each of the compounds as indicated. The Y-axis represents the Optical Density (OD) for the wavelength 590 nm, as an indication of the fluorescence MTT growth assay.

To determine the potential toxicity of bifunctional ITC compounds, human macrophages, isolated from human blood, were treated with several ITC compounds for 24 hours, and subsequently assayed for their viability by a fluorescence-based MTT metabolic assay. The fluorescence at OD 595 nm (i.e., the viability) of the human macrophages was determined in the presence and absence of Compounds 37, 45, or the control Compound 2. As shown in FIG. 4, for some compounds a growth-inhibitory effect was observed at approximately 32 µg/mL and for all of the compounds at a concentration of approximately 64 µg/ml. However, the MIC values towards the microorganisms were much lower than 32 µg/mL (e.g., ~1-4 µg/mL Compound 37). Therefore, these data demonstrate that the ITC compounds synthesized in the present study, at least in vitro, possess a reasonable therapeutic index.

Example 8

Toxicity of Selected ITC Compounds In Vivo

To determine the in vivo tolerance of the novel ITC compounds, Compounds 30, 37, 42 and 45 were administered to mice at a range of dosages up to 50 mg/kg. At the highest dose, no toxicity was observed in the treated mice.

Example 9

Activity of Certain ITC Compounds is Reduced by Culture Media

ITC compounds can react with amine- and thiol-containing components of the culture media with the formation of corresponding thioureas and dithiocarbamates. The effect of pre-incubation of Compound 37 in MHB medium on its inhibitory activity against *Bacillus cereus* was determined at an initial concentration equal to the MIC value. The results are summarized in FIG. 5. While no growth of the bacteria occurs upon immediate addition of the inhibitor, progressive growth is observed as a function of pre-incubation time. These data indicate that there is a decrease of inhibition potency caused by an interaction between the compounds and the culture media.

Example 9

Toxicity and Bacterial Growth Inhibitory Activity of Selected ITC Compounds in an In Vitro Infection Model ITC compounds (37, 40, 42 and 45) were used to treat human peritoneal macrophages infected with *Mycobacterium tuberculosis* H37Rv strain. Rifampicin was used as a control for this experiment. At concentrations ranging up to 1 µg/mL, Compound 45 exibited low cytotoxicity, similar to Rifampicin, and the growth inhibitory activity of Compound 45 was comparabale with the inhibition observed for Rifampicin. Experiments using compounds 37 and 42 gave similar results (at a Rifampicin concentration 1-10 µg/mL). However, these two compounds exhibited more toxicity.

Example 10

Antiviral Activity of ITC Compounds

Isolation of Peripheral Blood Mononuclear Cells ("PBMC") from Normal Donor (Leucopack)

Leucopack was obtained from New York Blood Center (NYBC). All steps were performed by sterile techniques in a biosafety hood. Ficoll-Paque was equilibrated to 20° C. For each buffy coat, 15 ml of lymphopaque was placed into each of four 50 cc polypropylene tubes. The buffy coat was emptied into a T75 flask. The volume was adjusted to 100 ml with room temperature ("Rt") HBSS and, after gentle mixing, 35 ml was layed over Ficoll-plaque in each of 50 cc tubes. After spinning at 1500 rpm for 45 minutes, about 25 ml of serum was removed from each tube. Cells harvested at the interface were placed into two new 50 cc tubes. The tubes were filled with Rt HBSS, gently inverted a few times, and spun at 1500 rpm for 7 minutes at Rt. The wash liquid was removed and pellet gently resuspended by tapping with finger. The pellets were combined into one tube and suspended with Rt HBSS. After centrifugation (1000 rpm, 7 min Rt) the cells were resuspended in HBSS and spun again. Supernatant was discarded, the cells were resuspended in PHA medium and seeded in T75 flask ($10^8$ PBMC in 50 ml PHA medium), and incubated for 48 h at 37° C. in 5% $CO_2$.

Effect of ITC Compounds on Viral Proliferation

The PBMC were scraped and transferred into a 50 cc tube and spun at 2000 rpm for 5 min. The supernatant was discarded and the cells were resuspended in growth medium to the concentration $2 \times 10^6$ PBMC/ml. The cells (0.5 ml) were distributed into 48 well plates. In one procedure, cells were incubated for 30 minutes at 37° C. with the tested ITC compound prior to the addition of 50 μl of 1:100 diluted suspensions of virus (92TH594) particles. In another procedure, the ITC compound and the virus were added simultaneously. After incubation for 24 hours at 37° C., the cells were spun down at 2500 rpm for 5 minutes and washed with FCS free RPMI 1640 medium. The procedure was repeated two times. After the final centrifugation 0.5 ml of fresh growth medium was replenished. After 3 days the growth medium was changed and incubation continued for another 3 days. The 100 ml sample was withdrawn and the level of p24 viral antigen was determined using commercial kit. The same procedure was performed with NCS untreated cells as negative control. The p24 value is directly proportional to the number of viral particles in the sample.

As shown in Table 5, all tested ITC compounds exhibit strong antiviral activity at low concentration.

TABLE 5

P24 values (pg/ml). Compound added to the cells before viral infection.

| Compound | Compound, μg/ml | | |
|---|---|---|---|
|  | 0 | 2.5 | 10 |
| #30 | $2.6 \times 10^5$ | 320 | 0 |
| #37 | $2.6 \times 10^5$ | 210 | 0 |
| #42 | $2.6 \times 10^5$ | 220 | 0 |
| #45 | $2.6 \times 10^5$ | 960 | 6 |

In the most cases, short preincubation with ITC compounds prior to viral infection, strongly increased their antiviral activity (compare Tables 5 and 6).

TABLE 6

P24 values (pg/ml). Compound added to the cells after viral infection.

| Compound | Conc. of compound μg/ml | | |
|---|---|---|---|
|  | 0 | 2.5 | 10 |
| #30 | $2.6 \times 10^5$ | 643 | 155 |
| #37 | $2.6 \times 10^5$ | 760 | 340 |
| #42 | $2.6 \times 10^5$ | 630 | 700 |
| #45 | $2.6 \times 10^5$ | 975 | 7 |

However no detectable difference was observed for compound #45, which suggests a different mode of action for this particular ITC. Generally, a concentration of ITC as low as 10 μg/ml completely inhibits viral proliferation, while the efficiency of viral growth suppression was about 99.9% at a concentration of 2.5 mg/ml (Table 5).

Toxic concentrations of ITC for human cells are much higher (see Example 7), which makes these compounds candidates for antiviral drugs.

Example 11

NMR Spectra for ITC Compounds

Compound 16. $H^1$ NMR (CD3Cl): 7.33-7.23 (q, J=8.4 Hz, 4H); ~4.7 (s, 2H).

Compound 19. $H^1$ NMR (CD3Cl): 8.08 (bs, 1H); 7.55 (d, J=7.8 Hz, 1H); 7.39 (d, J=8.1 Hz, 1H); 7.15-7.25 (m, 2H); 7.12 (d, J=2.4 Hz, 1H); 3.78 (t, J=2.4 Hz, 2H); 3.17 (t, J=6.9 Hz, 2H).

Compound 27. $H^1$ NMR (CD3Cl): 7.30-7.42 (m, 5H); 4.92 (q, J=6.9 Hz, 1H); 1.68 (d, J=6.6 Hz, 3H).

Compound 30. $H^1$ NMR (CD3Cl): 8.62 (d, J=4.8 Hz, 1H); 8.58 (s, 1H); 7.71 (d, J=8.1 Hz, 1H); 7.36 (dd, J=8.1 Hz, J=4.8 Hz, 1H); 4.76 (s, 2H).

Compound 31. $H^1$ NMR (CD3Cl): 8.54 (d, J=4.8 Hz, 1H); 8.50 (s, 1H); 7.66 (d, J=7.8 Hz, 1H); 7.28 (dd, J=7.8 Hz, J=4.8 Hz, 1H); 3.76 (t, J=6.9 Hz, 2H); 3.00 (t, J=6.9 Hz, 2H).

Compound 32. $H^1$ NMR (CD3Cl): 8.57 (d, J=4.8 Hz, 1H); 7.66 (t, J=7.8 Hz, 1H); 7.18-7.27 (m, 2H); 3.96 (t, J=6.6 Hz, 2H); 3.15 (t, J=6.6 Hz, 2H).

Compound 33. $H^1$ NMR (CD3Cl): 7.98-8.25 (m, 9H); 5.37 (s, 2H).

Compound 34. $H^1$ NMR (CD3Cl): 7.51 (s, 1H); 7.10 (s, 1H); 6.93 (s, 1H); 4.14 (t, J=6.6 Hz, 2H); 3.50 (t, J=6.3 Hz, 2H); 2.14 (quint, J=6.3 Hz, 2H).

Compound 35. $H^1$ NMR (CD3Cl): 3.15 (s, 2H); 2.04 (bs, 3H); 1.69 (q, J=12 Hz, 6H); 1.59 (d, J=2.7 Hz, 6H).

Compound 37. $H^1$ NMR (CD3Cl): ~7.35 (s, 4H); ~4.72 (s, 4H).

Compound 38. $H^1$ NMR (CD3Cl): 3.62 (m, 4H); 1.85 (m, 4H).

Compound 39. $H^1$ NMR (CD3Cl): 3.57 (t, J=6.6 Hz, 4H); 1.71-1.81 (m, 4H); 1.53-1.62 (m, 2H).

Compound 40. $H^1$ NMR (CD3Cl): 3.55 (t, J=6.6 Hz, 4H); 1.68-1.76 (m, 4H); 1.45-1.50 (m, 4H).

Compound 41. $H^1$ NMR (CD3Cl): 3.53 (t, J=6.6 Hz, 4H); 1.67-1.76 (m, 4H); 1.31-1.50 (m, 6H).

Compound 42. $H^1$ NMR (CD3Cl): 3.52 (t, J=6.6 Hz, 4H); 1.66-1.75 (m, 4H); 1.31-1.50 (m, 8H).

Compound 43. $H^1$ NMR (CD3Cl): 3.67-3.76 (m, 12H).

Compound 45. $H^1$ NMR (CD3Cl): 3.65 (t, J=6.6 Hz, 2H); 3.51 (t, J=6.6 Hz, 2H); 1.65-1.75 (m, 2H); 1.53-1.60 (m, 2H); 1.23-1.47 (m, 8H).

Compound 59. $H^1$ NMR (CD3Cl): 7.35 (d, J=8.4 Hz, 1H); 6.50 (d, J=8.4 Hz, 1H); 6.44 (s, 1H); 5.98 (s, 1H); 4.25 (bs, 1H); 3.54 (t, J=6.8 Hz, 2H); 3.19 (bs, 2H); 2.34 (s, 3H); 1.60-1.80 (m, 4H); 1.40-1.55 (m, 4H).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and script of the invention, and all such variations are intended to be included within the scope of the following claims.

What is claimed is:

1. A composition of matter according to Formula I:

or a pharmaceutically acceptable salt or thereof, wherein:
a is 1, b is 1, and c is 0 or 1;
- X is an aryl or heteroaryl ring system which may be unsubstituted or substituted with from 1 to 4 moieties selected from —Br, —Cl, —OH, —NH$_2$, —COOH, OR'—CH$_3$ or R"—CH$_3$ wherein R' and R", independently, are an alkylene moiety having the formula —(CH$_2$)$_n$—, where n can be an integer from 0 to 20; and
- each R, independently, is selected from the group consisting of linear or branched alkylene moieties having from 1 to 20 C atoms; linear or branched alkenylene and alkynylene moieties having from 2 to 20 C atoms; linear or branched heteroalkylene moieties having from 2 to 20 C atoms and from 1 to 3 O, N or S atoms; and heteroarylene, and cycloalkylene moieties having from 5 to 10 C atoms and from 1 to 3 N, S, or O atoms; provided that R is not —CH$_2$— when X is phenyl.

2. The composition of claim 1, where X is selected from phenyl, biphenyl, napthyl, anthrocyl, indole, pyrimidine, pyrene, furan, and pyridine.

3. The composition of claim 1, wherein each R, independently, is an alkylene moiety having the formula —(CH$_2$)$_n$—, where n can be an integer from 1 to 20.

4. The composition of claim 2, wherein the X is a phenyl ring.

5. The composition of claim 1, wherein R is an heteroalkylene moiety having the formula

—(CH$_2$)$_2$—O—(CH$_2$)$_2$—O—(CH$_2$)$_2$—.

6. The composition of claim 5, wherein c is 1.

7. The composition of claim 1, wherein
each R, independently, is selected from the group consisting of linear or branched alkylene moieties having from 1 to 20 C atoms and linear or branched heteroalkylene moieties having from 2 to 20 C atoms and from 1 to 3 O, N or S atoms.

8. The composition of claim 1, wherein
each R, independently, is linear or branched alkylene moieties having from 1 to 20 C atoms.

9. The composition of claim 1, wherein
each R, independently, is linear or branched heteroalkylene moieties having from 2 to 20 C atoms and from 1 to 3 O, N or S atoms.

10. A composition of matter according to Formula I:

or a pharmaceutically acceptable salt or thereof, wherein:
a and c are independently 0 or 1, b is 1;
- X is an aryl or heteroaryl ring system which may be unsubstituted or substituted with from 1 to 4 moieties selected from —Br, —Cl, —OH, —NH$_2$, —COOH, OR'—CH$_3$ or R"—CH$_3$ wherein R' and R", independently, are an alkylene moiety having the formula —(CH$_2$)$_n$—, where n can be an integer from 0 to 20; and
- each R, independently, is selected from the group consisting of linear or branched alkylene moieties having from 7 to 20 C atoms; linear or branched alkenylene and alkynylene moieties having from 2 to 20 C atoms; and linear or branched heteroalkylene moieties having from 2 to 20 C atoms and from 1 to 3 O, N or S atoms.

11. The composition of claim 10, wherein a and c are 0, and R is an heteroalkylene moiety having the formula

—(CH$_2$)$_2$—O—(CH$_2$)$_2$—O—(CH$_2$)$_2$—.

12. The composition of claim 10, wherein a and c are 0, and R is an linear alkylene having from 7 C atoms.

13. The composition of claim 10, wherein a and c are 0, and R is an linear alkylene having from 8 C atoms.

14. A composition of matter according to Formula I:

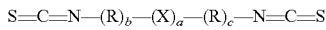

or a pharmaceutically acceptable salt or thereof, wherein:
a, b, and c are each 1;
- X is an aryl or heteroaryl ring system which may be unsubstituted or substituted with from 1 to 4 moieties selected from —Br, —Cl, —OH, —NH$_2$, —COOH, OR'—CH$_3$ or R"—CH$_3$ wherein R' and R", independently, are an alkylene moiety having the formula —(CH$_2$)$_n$—, where n can be an integer from 0 to 20; and
- each R, independently, is selected from the group consisting of linear or branched alkylene moieties having from 1 to 20 C atoms; linear or branched alkenylene and alkynylene moieties having from 2 to 20 C atoms; linear or branched heteroalkylene moieties having from 2 to 20 C atoms and from 1 to 3 O, N or S atoms; and arylene, heteroarylene, and cycloalkylene moieties having from 5 to 10 C atoms and from 1 to 3 N, S, or O atoms.

15. The composition of claim 14, wherein each R is independently a linear or branched alkylene moiety having from 1 to 20 C atoms, and X is an aryl ring system which may be unsubstituted or substituted with from 1 to 4 moieties selected from —Br, —Cl, —OH, —NH2, —COOH, OR'—CH3 or R"—CH3 wherein R' and R", independently, are an alkylene moiety having the formula —(CH2)n-, where n can be an integer from 0 to 20.

16. The composition of claim 14, wherein X is phenyl.

17. The composition of claim 14, wherein X is phenyl and R is CH$_2$.

* * * * *